United States Patent
Honda et al.

(10) Patent No.: US 6,963,035 B2
(45) Date of Patent: Nov. 8, 2005

(54) BODY WEIGHT MANAGING APPARATUS

(75) Inventors: Yuka Honda, Tokyo (JP); Katsumi Takehara, Tokyo (JP)

(73) Assignee: Tanita Corporation, Tokyo (JP)

(*) Notice: Subject to any disclaimer, the term of this patent is extended or adjusted under 35 U.S.C. 154(b) by 55 days.

(21) Appl. No.: 10/417,351

(22) Filed: Apr. 17, 2003

(65) Prior Publication Data

US 2004/0035611 A1 Feb. 26, 2004

Related U.S. Application Data

(63) Continuation-in-part of application No. 10/113,984, filed on Apr. 2, 2002, now abandoned, which is a continuation-in-part of application No. PCT/JP01/06577, filed on Jul. 31, 2001.

(30) Foreign Application Priority Data

Aug. 4, 2000 (JP) ........................................ 2002-237190
Jul. 24, 2001 (JP) ........................................ 2001-222691

(51) Int. Cl.$^7$ ............................. A61B 5/05; G01G 19/40
(52) U.S. Cl. ....................... 177/25.19; 368/10; 600/547; 128/920; 128/921
(58) Field of Search .......................... 177/25.13–25.17, 177/25.19; 600/547, 300; 368/10; 128/921, 920

(56) References Cited

U.S. PATENT DOCUMENTS

| | | | |
|---|---|---|---|
| 4,008,712 A | 2/1977 | Nyboer | 600/547 |
| 4,366,873 A | 1/1983 | Levy et al. | 177/25.19 |
| 4,423,792 A | 1/1984 | Cowan | 177/25.19 |

(Continued)

FOREIGN PATENT DOCUMENTS

| | | |
|---|---|---|
| DE | 28 25 095 A | 3/1980 |
| EP | 1 080 687 A1 | 3/2001 |
| EP | 1 114 610 A1 | 7/2001 |
| EP | 1 279 367 A1 | 1/2003 |
| FR | 2 731 144 A | 9/1996 |
| GB | 1 252 761 | 11/1971 |
| GB | 1 252 781 | 11/1971 |
| WO | WO 99/52425 A | 10/1999 |

OTHER PUBLICATIONS

Pivarnik, J. et al. "Effects on endurance exercise on metabolic water production and plasma volume" 1984 *Journal of Applied Physiology Respiratory Environment and Exercise Physiology bol.* 56, nr. 3 p. 613–618 XP 008033885.

*Primary Examiner*—Randy W. Gibson
(74) *Attorney, Agent, or Firm*—McDermott Will & Emery LLP

(57) ABSTRACT

Disclosed is a body weight managing apparatus comprising: a body weight measuring unit; a bioelectric impedance measuring unit; a body water content evaluation unit; and a health condition evaluation unit. According to the present invention, said body weight measuring unit measures a body weight of a person to be measured, said bioelectric impedance measuring unit applies an alternating current to a body of the person and measures a bioelectric impedance value, said body water content evaluation unit evaluates a body water content based on the bioelectric impedance value measured by said bioelectric impedance measuring unit, and said health condition evaluation unit evaluates a health condition of the person based on the measured body weight and the evaluation result from said body water content evaluation unit.

16 Claims, 15 Drawing Sheets

U.S. PATENT DOCUMENTS

| | | | | |
|---|---|---|---|---|
| 4,576,244 A | | 3/1986 | Zeigner et al. | 177/245 |
| 4,831,242 A | | 5/1989 | Englehardt et al. | 235/382 |
| 4,844,187 A | | 7/1989 | Jabero | 177/5 |
| 5,579,782 A | | 12/1996 | Masuo | 600/547 |
| 5,720,296 A | | 2/1998 | Cha | 600/554 |
| 5,788,643 A | * | 8/1998 | Feldman | 600/506 |
| 5,876,763 A | | 3/1999 | Montner et al. | 424/722 |
| 6,013,290 A | | 1/2000 | Weinsein et al. | 426/74 |
| 6,040,531 A | | 3/2000 | Miller-Kovach et al. | 177/25.16 |
| 6,088,615 A | | 7/2000 | Masuo | 600/547 |
| 6,095,949 A | | 8/2000 | Arai | 482/4 |
| 6,125,297 A | * | 9/2000 | Siconolfi | 600/547 |
| 6,256,532 B1 | | 7/2001 | Cha | 600/547 |
| 6,280,396 B1 | | 8/2001 | Clark | 600/547 |
| 6,308,096 B1 | | 10/2001 | Masuo | 600/547 |
| 6,321,112 B1 | | 11/2001 | Masuo | 600/547 |
| 6,354,996 B1 | * | 3/2002 | Drinan et al. | 600/300 |
| 6,369,338 B1 | | 4/2002 | Kimura | 177/25.16 |
| 6,400,983 B1 | | 6/2002 | Cha | 600/547 |
| 6,434,422 B1 | * | 8/2002 | Tomoda et al. | 600/547 |
| 6,538,215 B2 | * | 3/2003 | Montagnino et al. | 177/25.16 |
| 6,643,543 B2 | * | 11/2003 | Takehara et al. | 600/547 |
| 6,714,813 B2 | * | 3/2004 | Ishigooka et al. | 600/547 |

* cited by examiner

Enter personal number

No : ____

(b)

Enter personal data

Hight: _____ cm

Age : _____ year(s)

Sex : _____ 1.Male 2.Female (c)

Enter target body weight

_____ kg

Enter target time period

_____ day(s)

(d)

Current measurement 1. before exercise 2. after exercise (e)

| | |
|---|---|
| Current body weight | 63.50kg |
| To target body weight | −3.50kg |
| Current body water content | 38.10kg |

(f)

| | |
|---|---|
| Current body weight | 63.25kg |
| Weight transition this time | −250g |
| Extracellular fluid content transition | −220g |
| Intracellular fluid content transition | −10g |
| To target body weight | −3.25kg |
| Current body water content | 37.95kg |
| Favorable weight loss | |

| Body weight transition / Body water content transition | Not less than −4%/day / Not less than −1.8kg/week | −4%/day < Rate < 4%/day / −1.8kg/week < Volume < 1.8kg/week | Not less than 4% / Not less than 1.8kg |
|---|---|---|---|
| Not less than −2%/day | too lean & dehydration | dehydration | fat & dehydration |
| −2%/day < Transition rate < 2%/day | too lean | normal | fat |
| Not less than 2%/day | too lean & edema | edema | fat & edema |

```
Enter season period

___ month _____ day
              ⌠
       ___ month _____ day
```

(b)

```
Enter date of matches

__month__day      __month__day

__month__day      __month__day

__month__day      __month__day
```

BODY WEIGHT MANAGING APPARATUS

BACKGROUND OF THE INVENTION:

This application is a continuation-in-part of co-pending U.S. application Ser. No. 10/113,984 filed Apr. 2, 2002 now abandoned which is a continuation-in-part of Pct/JP01/06577, filed Jul. 31, 2001.

FIELD OF THE INVENTION

The present invention relates to a body weight managing apparatus using a bioelectric impedance value for helping a user to lose or gain his/her body weight to reach to a target body weight according to a program without any reverse affection to health.

DESCRIPTION OF THE PRIOR ART

Weight reduction is common among athletes or sport players. In some kinds of sports such as, for example, wrestling, boxing, judo, weight lifting, sports players compete with others according to a weight rank classification except for open-weight division, and the players in these kinds of sports attempt to reduce their body weights in order to participate in matches in lower weight ranks, even if only slightly, to compete with players of smaller physical build for successful results to be obtained, and besides, in such sports as gymnastics, rhythmic gymnastics, figure skating and the like, the sports player competes with others based on point rating where physical appearances should be highly counted for and players in these type of sports also try to reduce their body weights to make their physical appearances or figures better looking for the successful results to be obtained.

In this regard, the weight reduction of a sport player has typically been practiced instantly in a short period starting at a few days prior to a match or competition by way of a dieting restriction method such as reduced diet or fasting, a sweating method by taking a bath or sauna, or a method using specific medication such as a cathartic or diuretic, in addition to a hard training method for increasing an amount of exercise itself. Although typically the schedule of the match or competition should have been informed sufficiently in advance, it is quite difficult to practice the weight reduction according to a plan specified along with the schedule of the match or competition, and, as shown in FIG. 12, a rapid weight reduction is practically repeated before each match or competition in such conditions that after a match or competition having been finished, a player tends to take more than regular amount of nutrition for regaining his/her physical energy, to reduce the amount of training to give a rest to the body, and further to exhibit a rebound of the rapid weight loss, resulting in returning back to the original condition of the body weight as before the weight loss, and again as approaching to another match or competition, the similar rapid weight reduction is practiced.

However, it has been conventionally pointed that such rapid weight reduction might possibly trigger not only lighter symptoms such as sleep disorder, feeling of lassitude, feeling of irritation, but also serious conditions such as deterioration in muscular power, function of cardiovascular system, oxygen intake capacity, thermo-regulation ability or the like, which harm the player's health to a considerable degree both mentally and physically. There have been indeed many such cases reported including that a player who appeared in a match or competition with his/her body weight rapidly reduced resultantly had fallen into a problematic physical condition at that day and reversely deteriorated his/her athletic power, and thus finished with poor record, or that another player who had repeated a short-term rapid weight reduction and ultimately had a complete disorder with his/her health resulting in lost carrier as a sport player.

In this viewpoint, it has been desired that the weight reduction should not be carried out rapidly in a short period but practiced according to a schedule in order to accomplish the original goal that is to obtain a successful record without doing any harm to health.

On the other hand, it has been known that various kinds of values, such as a body water content related value or a body fat related value, effective in health management can be calculated from a bioelectric impedance value measured in a living body.

In the light of the above circumstances, an object of the present invention is to provide a body weight managing apparatus using bioelectric impedance values for helping a user to reduce or gain his/her body weight to reach to a target body weight according to a program without doing any harm to health.

SUMMARY OF THE INVENTION

According to an aspect of the present invention, there is provided a body weight managing apparatus comprising: a body weight measuring unit; a bioelectric impedance measuring unit; a body water content evaluation unit; and a health condition evaluation unit, whereby said body weight measuring unit measures a body weight of a person to be measured, said bioelectric impedance measuring unit applies an alternating current to a body of the person and measures a bioelectric impedance value, said body water content evaluation unit evaluates a body water content based on the bioelectric impedance value measured by said bioelectric impedance measuring unit, and said health condition evaluation unit evaluates a health condition of the person based on the measured body weight and the evaluation result from said body water content evaluation unit.

According to one embodiment of the present invention, said health condition evaluation unit evaluates based on body weight transition as measured for a period of plural days.

According to another embodiment of the present invention, said health condition evaluation unit evaluates based on body water content transition as measured for a period of plural days.

According to further embodiment of the present invention, said health condition evaluation unit evaluates based on body weight transition and body water content transition as measured for a period of plural days.

According to another aspect of the present invention, there is provided a body weight managing apparatus comprising: a body weight measuring unit; a body water content evaluation unit; and a health condition evaluation unit, whereby said body weight measuring unit measures a body weight of a person to be measured, said body water content evaluation unit evaluates body water content transition during an exercise, derived based on the body weight values measured before and after the exercise by said body weight measuring unit, and said health condition evaluation unit evaluates a health condition of the person based on the evaluation result from said body water content evaluation unit.

According to further aspect of the present invention, there is provided a body weight managing apparatus comprising:

a body weight measuring unit; a bioelectric impedance measuring unit; a body water content evaluation unit; an input unit; and a body weight estimation unit, whereby said body weight measuring unit measures a body weight of a person to be measured, said bioelectric impedance measuring unit applies an alternating current to a body of the person and measures a bioelectric impedance value, said body water content evaluation unit evaluates a body water content based on the bioelectric impedance value measured by said bioelectric impedance measuring unit, said input unit enters data relating to an exercise, and said body weight estimation unit estimates a body weight after the exercise based on the measured body weight and the data entered by said input unit.

According to one embodiment of the present invention, said input unit enters at least one of the data: temperature, time period of exercise and intensity of exercise.

According to yet further aspect of the present invention, there is provided a body weight managing apparatus comprising: a body weight measuring unit; a clock; an input unit; an arithmetic unit; and a setting unit, whereby said body weight measuring unit measures a body weight of a person to be measured, said clock provides a clocking function, said input unit enters a target body weight, a target date and a time period for exercise, said arithmetic unit produces a body weight managing data based on the difference between the body weight measured by said body weight measuring unit and the target body weight entered by said input unit, and the number of days remaining until the target date entered by said input unit, and said setting unit sets a first day of the time period of exercise as the target date if there is no target date entered.

According to one embodiment of the present invention, said first day of the time period of exercise is a start date of exercise season.

According to another embodiment of the present invention, said first day of the time period of exercise is a day on which a match or competition is conducted.

According to yet further aspect of the present invention, there is provided a body weight managing apparatus comprising: a body weight input unit; a bioelectric impedance measuring unit; a body weight water content evaluation unit, and a health condition evaluation unit, wherein said body weight input unit inputs a measured body weight of a person, said bioelectric impedance measuring unit applies an alternating current to a body of the person and measures a bioelectric impedance value, said body water content evaluation unit evaluates a body water content based on the bioelectric impedance value measured by said bioelectric impedance measuring unit, and said health condition evaluation unit evaluates a health condition of the person based on the measured body weight inputted by said body weight input unit and the evaluation result from said body water content evaluation unit.

According to one embodiment of the present invention, said health condition evaluation unit evaluates based on body weight transition as measured for a period of plural days.

According to another embodiment of the present invention, said health condition evaluation unit evaluates based on body water content transition as measured for a period of plural days.

According to further embodiment of the present invention, said health condition evaluation unit evaluates based on the combination of body weight transition and body water content transition as measured for a period of plural days.

According to yet further embodiment of the present invention, there is provided a body weight managing apparatus comprising, a body weight input unit; a body water content evaluation unit; and a health condition evaluation unit, wherein said body weight input unit inputs a measured body weight of a person, said body water content evaluation unit evaluates body water content transition during an exercise, derived based on the body weight values measured before and after the exercise and inputted by said body weight input unit, and said health condition evaluation unit evaluates a health condition of the person based on the evaluation result from said body water content evaluation unit.

According to yet further aspect of the present invention, there is provided a body weight managing apparatus comprising: a body weight input unit; a bioelectric impedance measuring unit; a body water content evaluation unit; a data input unit; and a body weight estimation unit, wherein said body weight input unit inputs a measured body weight of a person, said bioelectric impedance measuring unit applies an alternating current to a body of the person and measures a bioelectric impedance value, said body water content evaluation unit evaluates a body water content based on the bioelectric impedance value measured by said bioelectric impedance measuring unit, said data input unit enters data relating to an exercise, and said body weight estimation unit estimates a body weight after the exercise based on the measured body weight inputted by said body weight input unit and the data entered by said data input unit.

According to one embodiment of the present invention, said input unit enters at least one of the data: temperature, time period of exercise and intensity of exercise.

According to yet further aspect of the present invention, there is provided a body weight managing apparatus comprising: a first input unit; a clock; a second input unit; an arithmetic unit; and a setting unit; wherein said first input unit inputs a measured body weight of a person, said clock provides a clocking function, said second input unit enters a target body weight, a target date and a time period for exercise, said arithmetic unit produces a body weight managing data based on the difference between the measured body weight inputted by said first input unit and the target body weight entered by said second input unit, and the number of days remaining until the target date entered by said input unit, and said setting unit sets a first day of the time period of exercise as the target date if there is no target date entered.

According to one embodiment of the present invention, said first day of the time period of exercise is a start date of exercise season.

According to another embodiment of the present invention, said first day of the time period of exercise is a day on which a match or competition is conducted.

BRIEF DESCRIPTION OF THE DRAWINGS

Now the present invention will be described in more detail with reference to the preferred embodiments as illustrated in the accompanying drawings, in which:

FIG. 4 shows some examples of indications on a display screen in the first embodiment shown in FIG. 1;

FIG. 10 shows examples of indications on a display screen of the second embodiment;

DETAILED DESCRIPTION OF THE PREFERRED EMBODIMENTS

Figure 1:
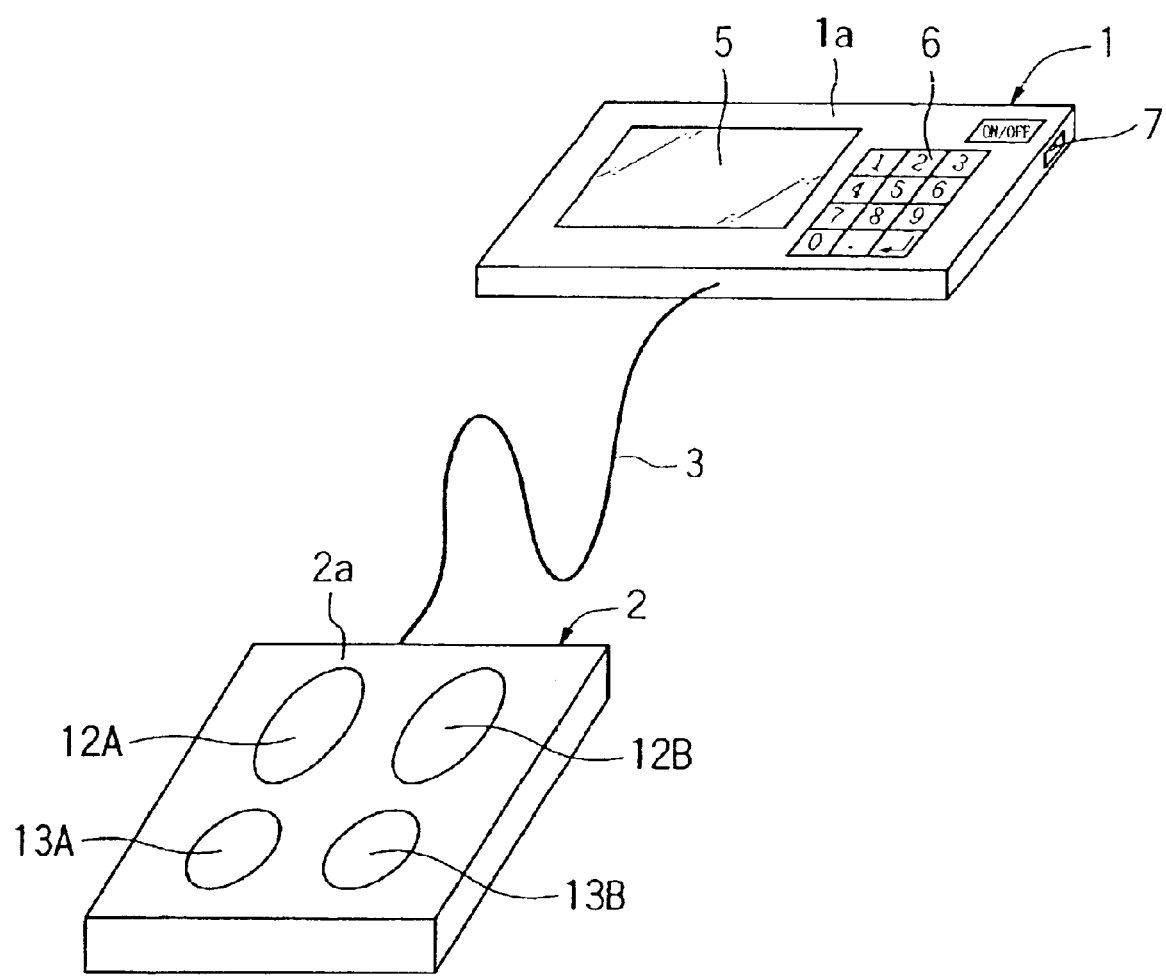
FIG. 1 is a perspective view illustrating an appearance of a body weight managing apparatus according to a first embodiment of the present invention.

Referring to FIG. 1, a body weight managing apparatus according to a first embodiment of the present invention is composed of a control section 1 for performing a display and a key input operation and a measuring section 2 for measuring a bioelectric impedance and a body weight, these sections being interconnected with a cable 3. A display section 5, a group of key switches 6 and an external I/O interface 7 are disposed on an outer surface of a housing 1a of the control section 1. Further, a pair of alternating current applying electrodes 12A and 12B and a pair of potential measuring electrodes 13A and 13B are disposed on an outer surface of a housing 2a of the measuring section 2.

Figure 2:
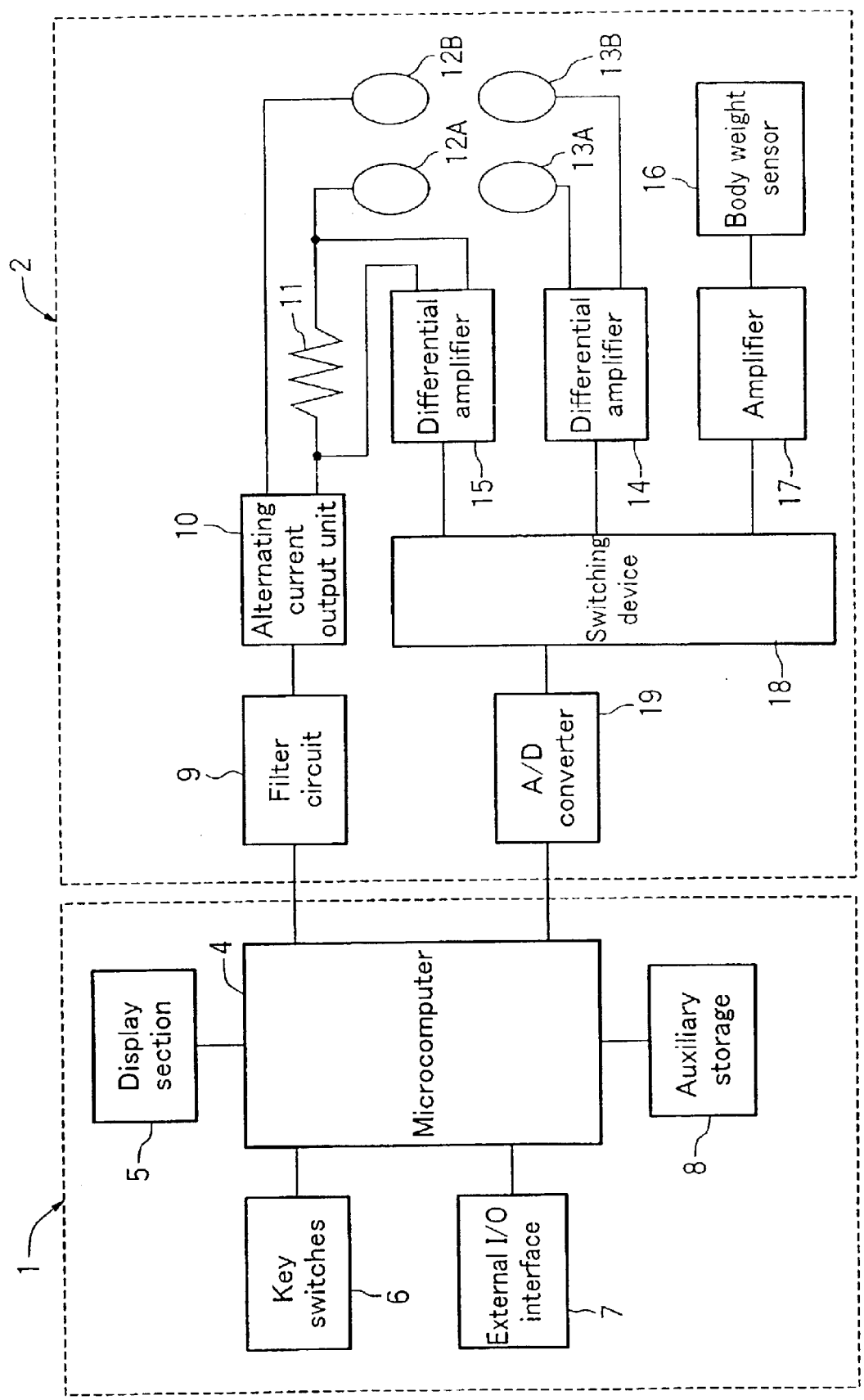
FIG. 2 is a schematic diagram illustrating a configuration of the first embodiment shown in FIG. 1.

FIG. 2 is a block diagram illustrating a configuration of the body weight managing apparatus shown in FIG. 1. This body weight managing apparatus is generally divided into the control section 1 and the measuring section 2 as described above, and said control section 1, as shown in FIG. 2, comprises a microcomputer 4 including: a CPU for performing a control and an arithmetic operations concerning to a measurement or the like; a ROM for storing a control and an arithmetic programs, constants and the like; a RAM for temporarily storing a calculated result, a program read from an external component, parameters and the like; and further a timer, a clock for generating date information, an I/O port and the like. Besides, the control section 1 further comprises: the display section 5 by means of a liquid-crystal display for indicating an personal parameter, a measured result, a measurement condition for a user, and the like; the key switch 6 used to input a control command to this managing apparatus and the personal parameter, and to select the personal parameter stored in an auxiliary storage 8; the external I/O interface 7 for performing an input-output operation to the external component; and the nonvolatile auxiliary storage 8 capable of storing, reading and updating the personal parameter, other parameters concerning to the measurement and the like.

On the other hand, the measuring section 2 comprises: a filter circuit 9 for forming a signal output from the microcomputer 4 into a signal to be applied to a living body; an alternating current output unit 10 for processing a signal output from the filter circuit 9 to generate a regulated effective value; a reference resistance 11 connected to one of output terminals of the alternating current output unit 10 for detecting a current flowing through the body of the user; the alternating current supply electrode 12A connected to one of the output terminals of the alternating current output unit 10 via the reference resistance 11 for applying a measuring current to the user; the alternating current supply electrode 12B connected to another one of the output terminals of the alternating current output unit 10 for applying a measuring current to the user; a differential amplifier 15 for detecting a potential difference between both ends of the reference resistance 11; potential measuring electrodes 13A and 13B for detecting potentials in two sites of the user; a differential amplifier 14 connected to the potential measuring electrodes 13A and 13B for detecting a potential difference between those electrodes; a body weight sensor 16 for measuring the body weight of the user; an amplifier 17 for amplifying an output from the body weight sensor 16; a switching unit 18 for selecting and outputting either one among those outputs from the differential amplifiers 15 and 14 and the amplifier 17 based on a control by the microcomputer 4; an A/D converter 19 for converting an analog signal representative of an output from the switching unit 18 into a digital signal and outputting said digital signal to the microcomputer 4.

Figure 3:
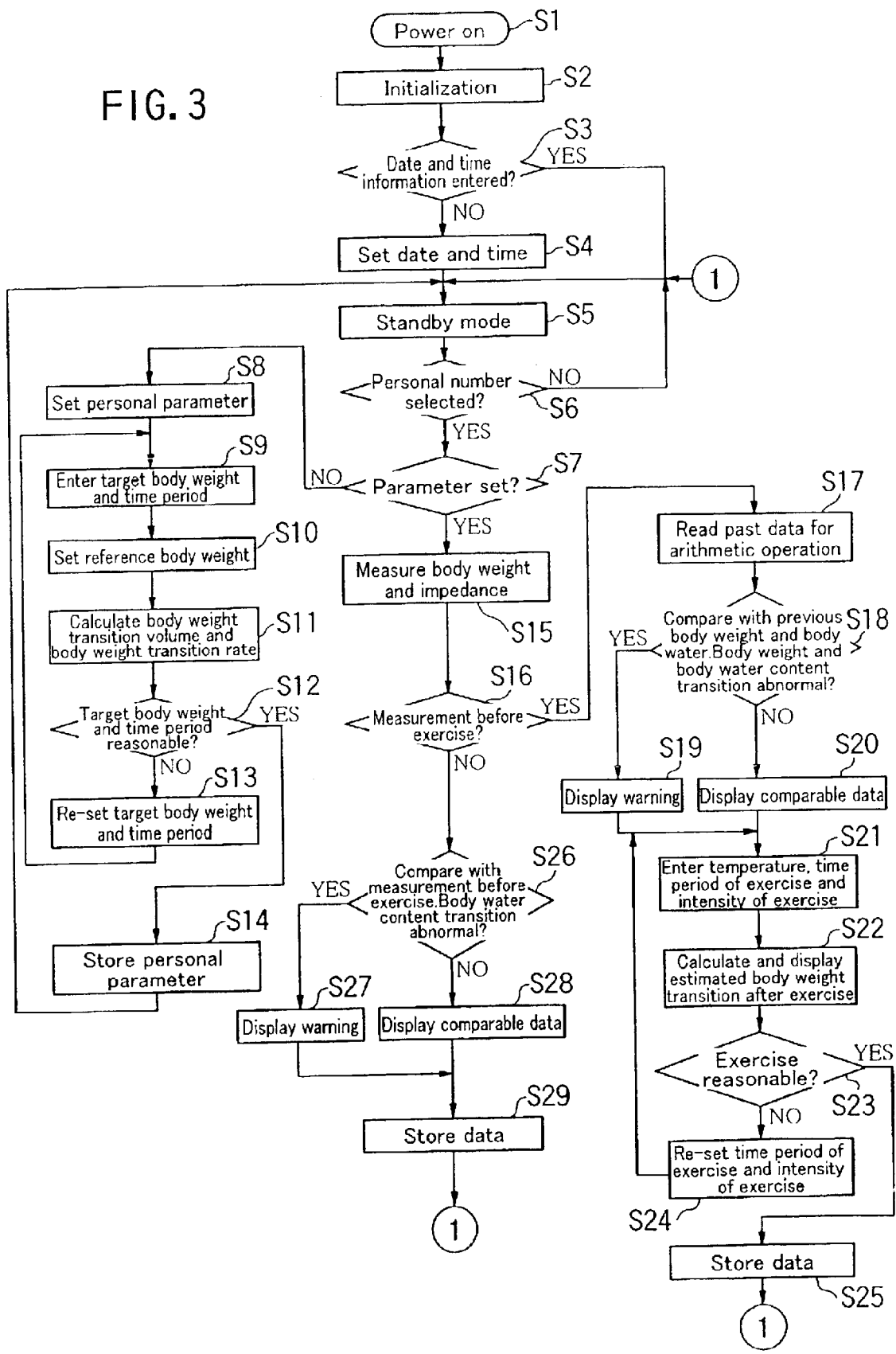
FIG. 3 is a flow chart illustrating an operational flow in the first embodiment shown in FIG. 1.

An operation of the body weight managing apparatus will now be described. FIG. 3 is a flow chart illustrating an operational flow of the first embodiment. When a user presses down an ON/OFF button of a power switch of a group of key switches 6 at Step S1, the managing apparatus initializes the internal components at Step S2, and after finishing the initialization, the apparatus checks to determine if date and time have been set or not at Step S3. If so, the apparatus enters a standby mode at Step S5, but if not, the apparatus sets the date and time at Step S4 and then enters the standby mode at Step S5. In the standby mode the apparatus displays on the screen of the display section 5 an indication requesting the user to input his/her personal number, as shown in FIG. 4(a).

At Step S6, the apparatus checks to determine if the user has entered the personal number using the key switches 6. If so, the managing apparatus determines whether any personal parameter corresponding to the entered personal number has been set in a memory area of the auxiliary storage 8 at Step S7. But, if not, the apparatus enters a parameter setting mode at Step S8 to display an indication on the screen of the display section 5 requesting the user to input his/her personal parameter, as shown in FIG. 4(b). When the user uses the group of key switches 6 to enter his/her height, age, and sex as the personal parameter, the managing apparatus further displays at Step S9 on the screen of the display section 5 an indication to request the user to enter a target body weight and a target time period to reach to said target body weight, as shown in FIG. 4(c). When the user enters the target body weight and the time period with the group of key switches 6, then at Step S10, the apparatus displays on the screen of the display section 5 an indication to request the user to step on the measuring section 2, and when the user put his/her body on the measuring section 2, the body weight sensor 16 measures the body weight of the user. Hereafter, said body weight is referred to as "a reference body weight".

Subsequently, the managing apparatus determines an average volume of body weight transition per week and an average rate of body weight transition per day from the measured reference body weight and the entered target body weight and target time period, at Step S11, by using the following equation:

An average body weight transition volume/week=((Target body weight−Reference body weight)÷Target time period)× 7(kg); and An average body weight transition rate/day=((Target body weight−Reference body weight)÷Target time period) ÷Reference body weight×100(%).

Then, at Step S12, the managing apparatus uses those values as a determination parameter to determine whether or not the entered target body weight and target time period are unreasonable values, that is to say, whether or not this is an unreasonable weight reduction or gain. It is to be noted that for the purpose of illustration in the present specification, the term "unreasonable" means "hazardous to health or unfavorable for health", unless otherwise specified. This determination is made based on such a criterion that, for example, an absolute value greater than 4% for the average body weight transition rate per day or an absolute value greater than 1.8 kg for the average body weight transition volume per week implies that the weight reduction or gain with the entered target body weight and time period is unreasonable. Then, when the apparatus has determined those are unreasonable values, the managing apparatus displays on the screen of the display section 5 an indication for giving a warning for this situation together with an ideal number of days required to reduce the body weight to the targeted body weight without any troubles, at Step S13. The ideal number of days may be calculated as, for example, a number of days required to reach to a targeted body weight where the average body weight transition rate per day is set at −4% or +4%, which is threshold value defining an acceptable range considered to be reasonable. Then, the present managing apparatus returns to Step S9, where it requests the user to enter another target body weight and another time period.

On the other hand, when it has been determined that those values are not unreasonable at Step S12, the managing apparatus calculates the average body weight transition volume per day and indicates said value as a target weight reduction value or a target weight gain value on the screen of the display section 5. Then at Step S14, the managing apparatus stores the personal parameter, the target body weight and the target time period, and the reference body weight in the memory area of the auxiliary storage 8 corresponding to the previously entered personal number, and thereafter, those data should be managed for each user. It is to be noted that although a summarized expression "to be stored in the auxiliary storage 8" will be used in the following description for the purpose of simplicity, the present managing apparatus, in principle, also similarly stores other data including any measured results and calculated results obtained in the processes as will be described below into the memory area of the auxiliary storage 8 corresponding to the personal number, which will be managed for each user. After having stored these data in the auxiliary storage 8, the managing apparatus returns to Step S5 to enter the standby mode.

On the other hand, when it has found that the personal parameter has been set in the auxiliary storage 8 at Step S7, the managing apparatus enters a measuring mode at Step S15. As the user brings his/her body onto the measuring section 2 with his/her toe portions of bottoms of left and right feet in contact with the alternating current supply electrodes 12A and 12B respectively and his/her heel portions of bottoms of left and right feet in contact with the potential measuring electrodes 13A and 13B respectively, the managing apparatus detects that the user has put his/her body onto the measuring section 2 by the body weight sensor 16, and starts to measure the body weight and the multi-frequency bioelectric impedance.

The multi-frequency bioelectric impedance measurement will now be described in brief. The multi-frequency bioelectric impedance measurement is a measuring method of the bioelectric impedance in which the measurement is carried out "n" times for each of "n" differently specified frequencies "Fi" (i=1 to n, where n is a predetermined set value). Initially, i=1 is set, and the first time measurement of the bioelectric impedance value is started for the predetermined frequency F1. That is to say, an output signal frequency is set in the filter circuit 9 based on a measurement control parameter which has been stored in advance in the ROM in the microcomputer 4, and an output signal having that frequency is output to the alternating current output unit 10 from the filter circuit 9. The alternating current output unit 10 comprises a constant-current output circuit for which a desired current value can be set. An output current value is set in the alternating current signal output unit 10 based on the measurement control parameter, and an alternating current output of said output current value is applied to the user through the alternating current supply electrode 12A being in contact with the user, which is connected to one of the output terminals of the alternating current signal output unit 10 via the reference resistance 11, and also through another alternating current supply electrode 12B connected to the other output terminal of the alternating current signal output unit 10. During the current being applied to the user, potentials at two sites in the body of the user are detected by a pair of potential measuring electrodes 13A and 13B being in contact with the user, and outputs of those potentials are fed to the differential amplifier 14. The differential amplifier 14 outputs a potential difference signal between those 2 sites. Further, during the current being applied to the user, the differential amplifier 15 outputs a potential difference signal for the reference resistance 11. Those potential difference signals from the differential amplifiers 14 and 15 are sent to the A/D converter 19 by switching the switching unit 18 through the control signal from the microcomputer 4. The A/D converter 19 converts these received analog signals to digital signals, which in turn are sent to the microcomputer 4, and the microcomputer 4 determines a bioelectric impedance value from the received digital signals and stores said value in the RAM.

After the first time measurement of the bioelectric impedance value having been finished, the present managing apparatus increments "i" by 1, as i=i+1, and determines whether or not the "i" is greater than the predetermined value "n". Then, if "i" is greater than "n", the measurements of the bioelectric impedance values are all completed, and if not, the measurement of the bioelectric impedance is performed for the next new frequency.

After the multi-frequency bioelectric impedance measurements having been carried out as described above, then the managing apparatus calculates an impedance vector locus and a related value of parameter from the bioelectric impedance value that has been measured for each of a plurality of different frequencies.

Figure 6:
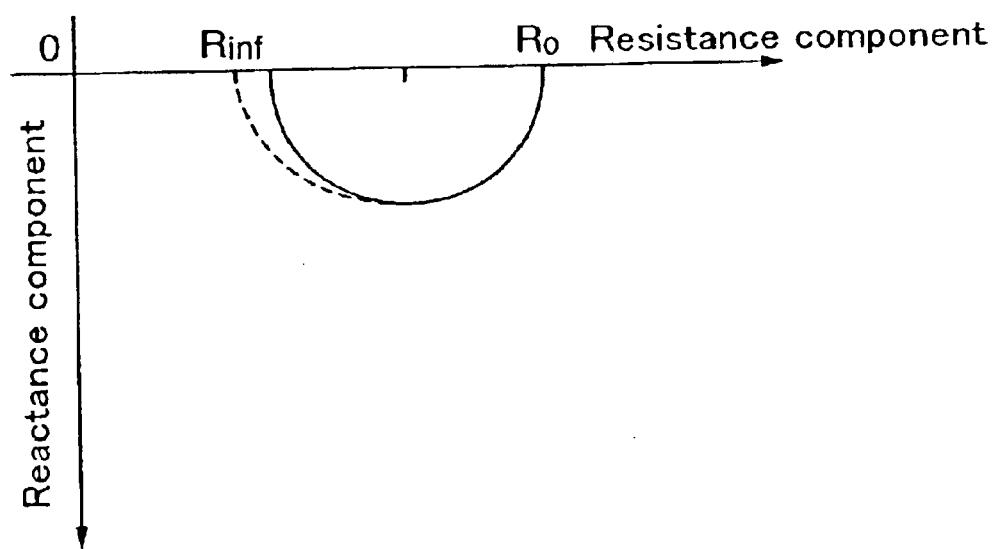
FIG. 6 is a diagram illustrating a bioelectric impedance vector locus of a human body.

The method for calculating the impedance vector locus and the related value of parameter will now be described in brief. Although the bioelectric impedance value is typically described by the equivalent circuit by way of lumped constants composed of an extracellular fluid resistance "Re", an intracellular fluid resistance "Ri" and a cell membrane capacity "Cm", each of cells constructing a living body is actually explained by a circuit having different constants respectively depending on its shape and nature, and therefor in the living body as an aggregate of those cells, the impedance vector locus would not draw a semi-circular arc as is the case where the equivalent circuit by way of the lumped constants is measured but would draw a circular arc according to the Cole-Cole circular arc law. Accordingly, the impedance of the living body generally makes a locus of circular arc shown in FIG. 6. In FIG. 6, a resistance component of an impedance is represented by the lateral axis, while a reactance component of the impedance is represented by the longitudinal axis. Since the reactance component of the bioelectric impedance is of capacitive type, it takes a negative value and its vector locus appears in the quadrant below the real axis as shown in FIG. 6.

Figures 7, 8:
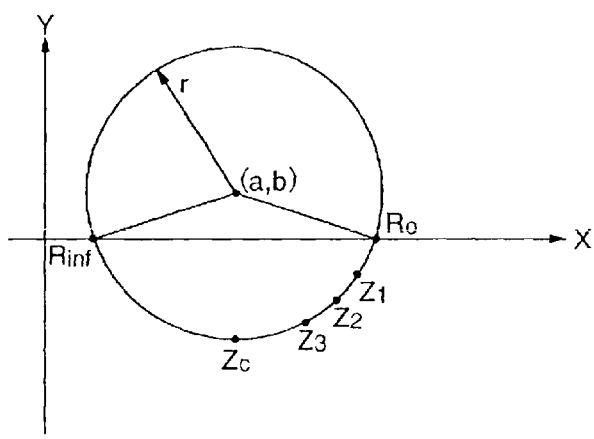
FIG. 7 is a diagram illustrating a relationship between bioelectric impedance at a frequency of 0 Hz and at a frequency of infinity and a bioelectric impedance at a characteristic frequency.
FIG. 8 is an evaluation matrix for body weight transition and body water content transition on the basis of which an evaluation of health condition is conducted.

Based on the assumption that the vector locus of the interest is the circular arc, respective bioelectric impedance values Z1, Z2, . . . Zn measured respectively at the "Fi" frequencies (i=1 to n) are represented at those points as shown in FIG. 7. The following description uses "X" axis defining the lateral axis representative of the real axis and "Y" axis defining the longitudinal axis representative of the imaginary axis of the impedance vector plane as shown in FIG. 6.

The following correlation function is obtained from Z is (i=1 to n) plotted on the coordinate.

$$(X-a)^2 + (Y-b)^2 = r^2 \quad \text{(Equation 1)}$$

In the above equation 1, "a" represents an X coordinate of the center of the circle, "b" represents a Y coordinate of the center of the circle and "r" represents a radius of the circle, and the equation 1 is, namely, an approximate correlation expression. Then, from the equation 1, obtained is:

$$X = a \pm \sqrt{(r^2 - b^2)}$$

and, further since $R0 > R_{inf}$, obtained are:

$$R0 = a + \sqrt{(r^2 - b^2)},$$

$$R_{inf-a} - \sqrt{(r^2-b^2)}$$

Figure 5:
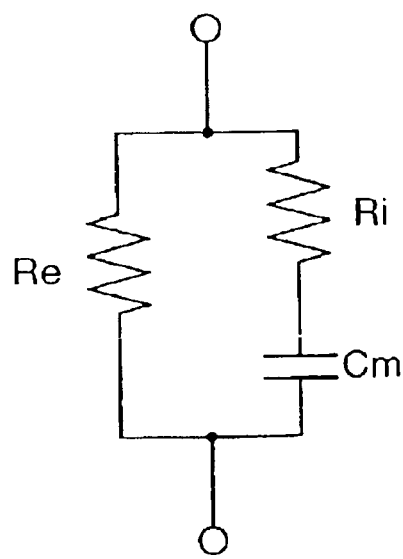
FIG. 5 is an electrically equivalent circuit diagram of cells in a tissue.

Based on these result, Re and Ri in the equivalent circuit of FIG. 5 is determined as follows:

$$Re = R0$$

$$Ri = R0 ER_{inf}/(R0 - R_{inf})$$

From the above arithmetic operation, there are obtained the combined intracellular and extracellular fluid resistance $R_{inf}$ (=Ri//Re), the extracellular fluid resistance Re, the intracellular fluid resistance Ri, and the ratio of either one of those to another one of those.

Further, using a known arithmetic method and based on the determined impedance vector locus, the related values of parameter, R0 and $R_{inf}$, or Re and Ri, and the sex, height and age that have been entered as the personal parameter at Step 6, and also the body weight measured at the present step, the intracellular fluid content ICW, extracellular fluid content ECW, body water content TBW=ICW+ECW, the ratio of either one of those to another one of those may be determined. For example, the intracellular fluid content ICW, the extracellular fluid content ECW, the body water content TBW may be determined from Ri, Re, height Ht and weight W by using the following equations:

$$ICW = K_{i1} Ht^2 / Ri + K_{i2} W + K_{i3}$$

$$ECW = K_{e1} Ht^2 / Re + K_{e2} W + K_{e3}$$

$$TBW = ECW$$

(where, $K_{i1}$, $K_{i2}$, $K_{i3}$, $K_{e1}$, $K_{e2}$, and $K_{e3}$ are coefficients).

By way of the calculation method described above, the managing apparatus calculates especially the intracellular fluid content, the extracellular fluid content and the body water content to be used in the processes as will be described below. Because of the multi-frequency bioelectric impedance measurements already known in the art a part of the description has been omitted.

Subsequently at Step S16, the managing apparatus displays on the screen of the display section 5 an indication to ask the user whether the current measurement is implemented before the exercise or after the exercise, and when the user uses the key switches 6 to give a response indicating that the measurement is implemented before the exercise, then the apparatus reads the past data for an arithmetic operation, at Step S17. This produces an evaluation parameter that is used at Step S18 for evaluating the health condition measured before the exercise. The evaluation of the health condition at Step S18 is conducted depending on body weight transition and body water content transition. Referring to FIG. 8 showing an evaluation matrix for body weight transition and body water content transition, if the health condition corresponding to any position other than "Normal" lasts for a period of more than the predetermined interval, for example, three days, then it means that the health condition is abnormal. In other words, if the measurement result corresponds to any one of the conditions "too lean & dehydration", "too lean", "too lean & edema", "dehydration", "edema", "fat & dehydration", "fat", and "fat & edema" in the matrix of FIG. 8, and the condition lasts for a period of more than three days, then the health condition is determined to be abnormal. On the other hand, if the condition lasts for a period of less than three days, but it changes in position in the matrix, then the condition is considered simply as temporal matter, and therefore, it is not determined to be abnormal.

Such evaluation of the health condition is conducted at Step S18, and therefore, at Step S17, the past data is read in for performing the following arithmetic operation:

The body weight transition rate per day and the body weight transition volume per week may be used as the parameters for determining the condition of the body weight transition. These parameters for the determination may be derived from the currently measured body weight before the exercise and the previously measured body weight before the exercise or the like that have been stored in the auxiliary storage 8, by the following equations:

Body weight transition rate/day=(Currently measured body weight before the exercise −Previously measured body weight before the exercise)/Reference body weight×100 (%), and Body weight transition volume/week=Average body weight before the exercise measured for last one week−

Average body weight before the exercise measured for one week prior to the last one week (kg).

If the body weight before the exercise was not measured in the previous day, the last body weight before the exercise among those body weights before the exercise measured in the past may be used to determine the body weight transition rate, and in this case, the result should be divided by the number of days between the day of the last measurement and the day of the current measurement to determine the body weight transition rate per day.

The evaluation of the condition of the body weight transition is made based on such a criterion that, for example, if the body weight transition rate/day is more than −4% it is considered to be "too lean", but if the body weight transition rate/day is more than +4% it is considered to be "fat". In addition, if the body weight transition volume/week is more than −1.8 kg it is considered to be "too lean", but if the body weight transition volume/week is more than +1.8 kg it is considered to be "fat". The condition other than those is considered to be "normal".

In the same manner, the body water transition rate/day is used as the evaluation parameter for evaluating the condition of body water transition. This evaluation parameter is derived from the currently measured body water content before the exercise and the previously measured body water content before the exercise or the like that have been stored in the auxiliary storage 8, by the following equations:

Body water content transition rate/day=(Currently measured body water content before the exercise−Previously measured body water content before the exercise)/Previously measured body water content before the exercise×100 (%)

If the body water content before the exercise was not measured in the previous day, the last body water content before the exercise among those body water content before the exercise measured in the past may be used to determine the body water content transition rate, and in this case, the result should be divided by the number of days between the day of the last measurement and the day of the current measurement to determine the body water content transition rate per a day.

The evaluation of the condition of the body water content transition is made based on such a criterion that, for example, if the body water content transition rate/day is more than −2% it is considered to be "dehydration", but if the body water content transition rate/day is more than +2% it is considered to be "edema". The condition other than those is considered to be "normal".

Then, if the body condition is determined abnormal at Step S18, the managing apparatus displays on the screen of the display section 5 the determined result along with a warning that the condition of the body weight transition and body water content transition is abnormal at Step S19. On the other hand, if the body condition is determined normal, the apparatus displays, at Step S20, on the screen of the display section 5 the body weight measured at this time, the difference between this body weight and the targeted body weight, and the body water content measured at this time, as shown in FIG. 4(e), which display means that the body condition is normal.

Then, when the user uses the key switches 6 to enter an ambient temperature in the place where the user is going to take an exercise, a time period of the exercise and an intensity of the exercise as an exercise condition, at Step S21, the managing apparatus estimates a body weight transition volume between the body weights before and after the current exercise to be taken under the currently entered exercise condition, based on the previously entered exercise condition and previously experienced body weight transition volume between the body weights before and after the exercise taken under said previously entered exercise condition, which have been stored in the auxiliary storage 8, and at Step S22, the managing apparatus displays on the screen of the display section 5 the estimated body weight transition volume.

Then the apparatus determines whether the exercise is reasonable or not at Step S23. This determination is made based on such a criterion that, for example, the exercise is reasonable if the estimated body weight transition rate is in the range of ±2%. If the apparatus determines that the exercise is unreasonable then the apparatus requests the user to perform re-setting of the time period and the intensity of exercise, at Step S24. Therefore, the use re-enters the time period and the intensity of exercise, at Step S21. On the other hand, if the apparatus determines that the exercise is reasonable, at Step S23, then it stores the body weight measured at this time, the bioelectric impedance value, and the body water content, the intracellular fluid content, the extracellular fluid content or the like that have been calculated from the bioelectric impedance value in the auxiliary storage 8, as Step S25.

On the other hand, when the user uses the key switches 6 to return a response indicating that the measurement is implemented after the exercise, at Step S16, then the apparatus evaluates the physical condition at the present point of time as measured after the exercise at Step S26. At this Step, the apparatus evaluates particularly a condition of the body water content for determining the health condition, that is to say, the apparatus determines whether or not any dehydration or edema conditions have occurred. Typically, the body weight transition such as the weight loss or gain tends to trigger an abnormal condition of the body water content such as edema or dehydration, and it has been said that the edema condition is one of the main symptoms of serious disease and the dehydrated condition is a main factor in various symptoms caused by the weight loss as described above. Accordingly, particularly in the body weight transition period, the condition of the body water content has important implications for one's health.

As an evaluation parameter for evaluating the condition of the body water content, a body weight transition rate between the body weights before and after the exercise for the measurement and an evaluation level may be used. The body weight transition rate for before to after the exercise may be calculated by using the body weights measured before and after the exercise, from the following equation:

Body weight transition rate=(Currently measured body weight after the exercise−Previously measured body weight before the exercise)/Reference body weight×100(%).

The reason why the body weight transition rate for before to after the exercise is employed for the evaluation parameter at this Step comes from the fact that the body weight transition for before to after the exercise is mostly due to the body water content transition and accordingly it can be considered that the body water transition volume for before to after the exercise is substantially the transition volume in body water content. Herein, it is not necessarily agreed that the transition volume in the body weight in a period other than the period for before to after the exercise is due to the transition in the body water content, and therefore it should be noted that it is not appropriate for the transition volume in the body weight for the period other than the period for before to after the exercise to be used as the evaluation parameter for determining the condition of the body water content.

On the other hand, the evaluation level is determined based on the body water content transition rate, and the body water content transition rate may be calculated by using the body water content after the exercise determined from the bioelectric impedance value currently measured after the exercise and the body water content before the exercise determined from the bioelectric impedance value previously measured before the exercise, from the following equation:

Body water content transition rate for before to after the exercise=(The body water content currently measured after the exercise−The body water content previously measured before the exercise)/The/body weight previously measured before the exercise×100(%).

Then, based on the resultant body water content transition rate for before to after the exercise, the evaluation level may be determined in such a way that, for example, the body water content transition rate within a range of −2% to +2% implies the condition of the body water content being normal and the evaluation level is defined as level 0, that the body water content transition rate greater than +2% and the previous body water content transition rate lower than +2% implies a transient edema condition and the evaluation level is defined as level 1, that both of the current and the previous body water content transition rates greater than +2% implies a chronic edema condition and the evaluation level is defined as level 2, that the body water content transition rate lower than −2% and the previous body water content transition rate not lower than −2% implies a transient dehydrated condition and the evaluation level is defined as level −1, and that both of the current and the previous body water content transition rates lower than −2% implies a chronic dehydrated condition and the evaluation level is defined as level −2.

The evaluation of the condition in body water content is based on such a criterion that the body weight transition rate below −2% or greater than +2% or the evaluation level of −2 or +2 determines the condition abnormal in body water content. Then, if it is determined abnormal, the present managing apparatus displays on the screen of the display section 5 a determined result together with a warning of the condition abnormal in body water content at Step S27.

On contrast, if it is determined to be normal at Step S26, the managing apparatus, at Step S28, displays on the screen of the display section 5 the currently measured body weight, the difference between this body weight and the targeted body weight, the currently measured body water content and the like as shown in FIG. 4(f), and this indication substitutes for the notification of the condition being normal. Then at Step S29, the currently measured body weight value, bioelectric impedance value, body water content determined from the bioelectric impedance value, intracellular fluid content, extracellular fluid content and the like are stored in the auxiliary storage 8. The measurement after the exercise is thus completed.

Figure 9:
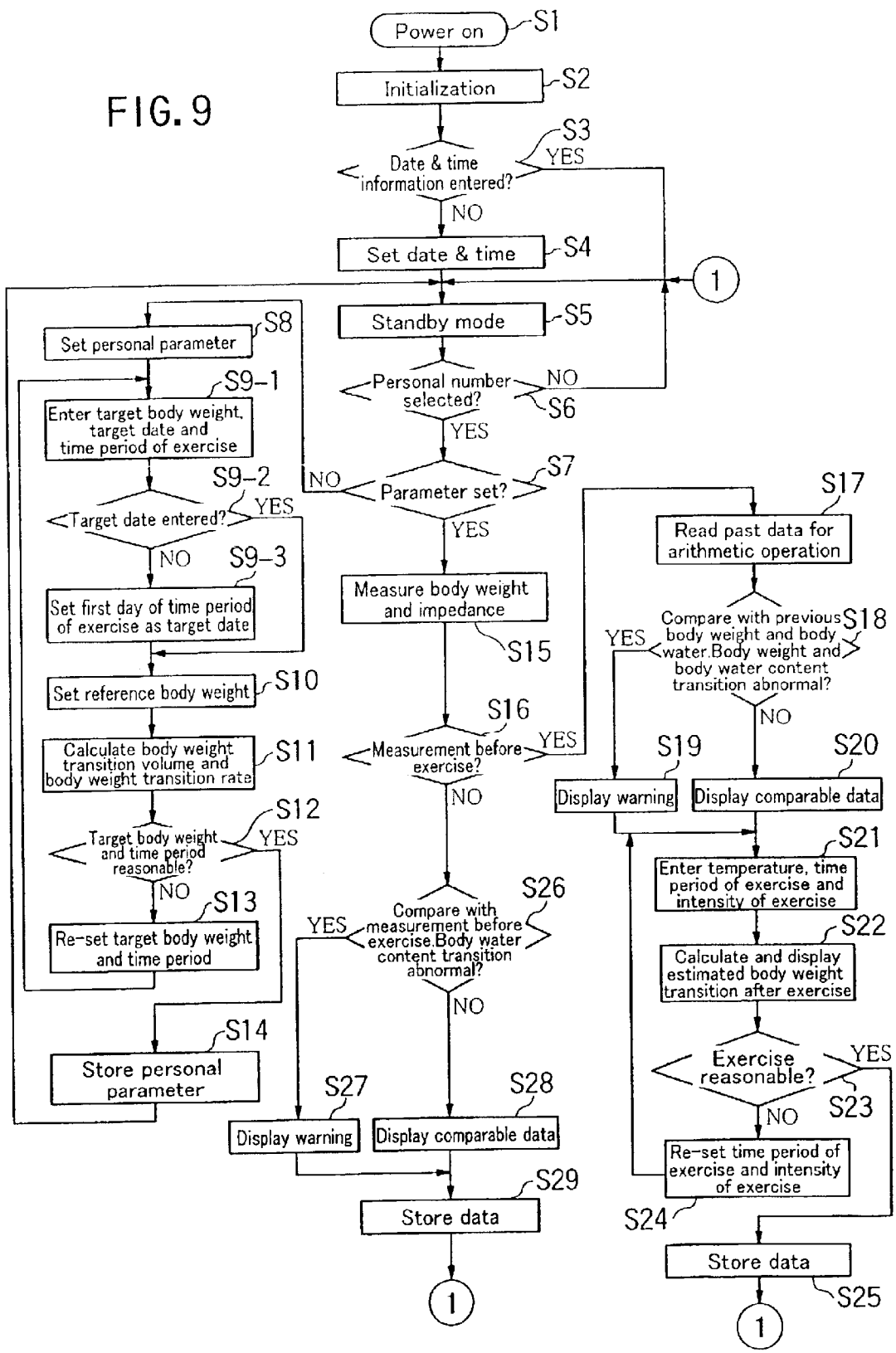
FIG. 9 is a flow chart illustrating an operational flow in a second embodiment.

There will now be described a second embodiment of the body weight managing apparatus according to the present invention. The present body weight managing apparatus is provided in order to use in managing a body weight of a sport player for a long time period, for example, for a year. An exterior appearance and configuration of the present managing apparatus are similar to those of the first embodiment, and the explanation on those will be omitted. Further, an operational flow in the present managing apparatus is almost similar to that of the first embodiment as shown in FIG. 3, except for the contents of some steps, and those different points will be specifically explained below with reference to the flow chart illustrated in FIG. 9. The difference between the flow chart in FIGS. 3 and 9 is only that Step S9 in FIG. 3 is replaced with Steps S9-1, 9-2 and 9-3 in FIG. 9.

Figure 11:
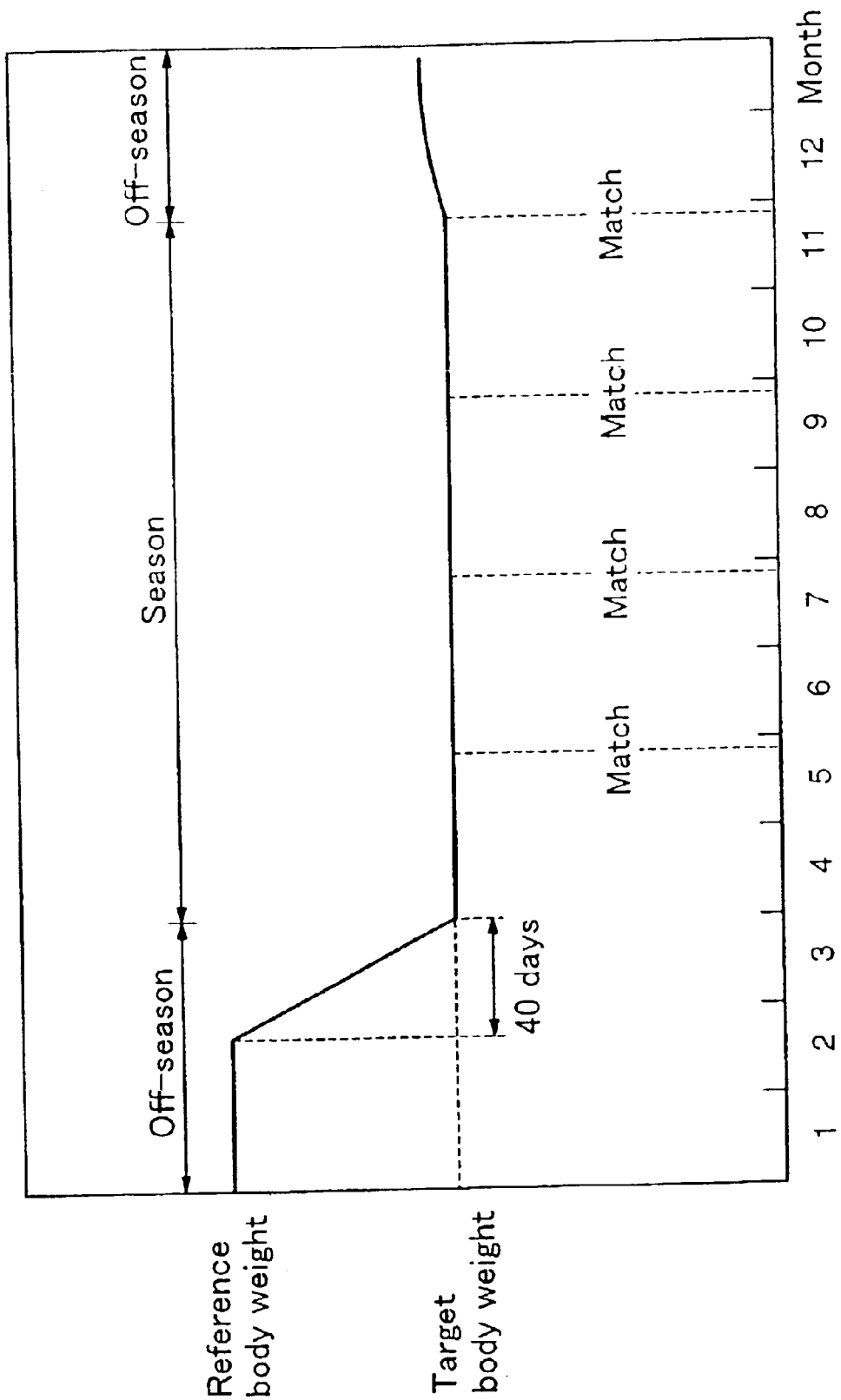
FIG. 11 is a diagram showing an example of a preferred body weight transition curve of the second embodiment.
Figure 12:
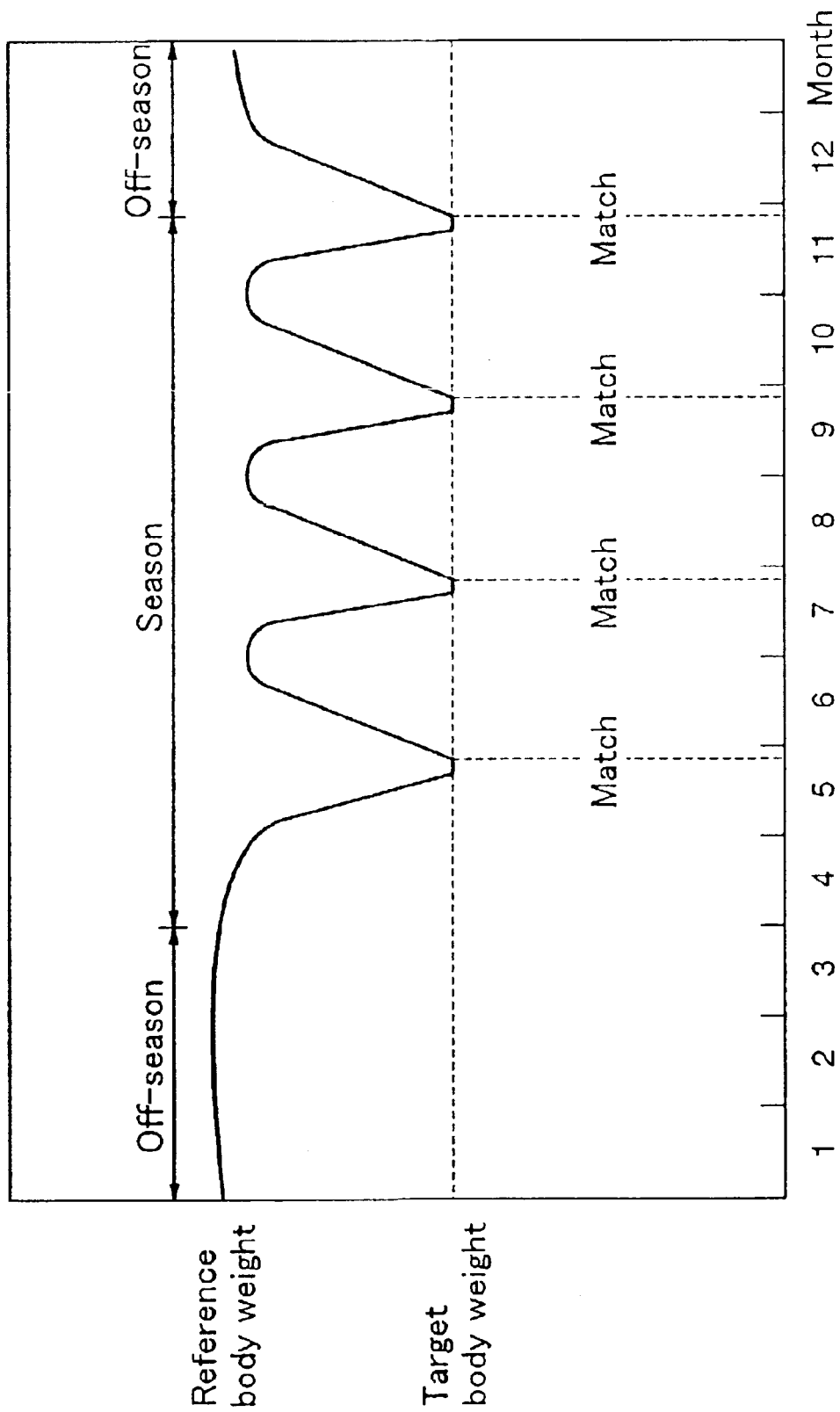
FIG. 12 is a diagram showing an example of a body weight transition curve in a conventionally practiced weight reduction scheme.

The managing apparatus, at Step S9-1, displays on the screen of the display section 5 an indication to request a user to enter a schedule relating to the matches or competitions, that is, a season for the matches or competitions (or time period of exercise), dates of matches (or target dates) and a target body weight, as shown in FIGS. 10(a) and (b). When the user uses a group of key switches 6 to enter the schedule relating to the matches or competitions then the managing apparatus determines whether the target date is entered or not, at Step S9-2. If not, the apparatus sets a first day of the time period of exercise as the target date, at Step S9-3. Thereafter, the apparatus measures the reference body weight at Step S10 in the similar manner to the first embodiment. Then, at Step S11, the apparatus generates an ideal body weight managing program by the microcomputer 4 based on the entered schedule relating to the matches or competitions to achieve the target body weight according to the schedule relating to the matches or competitions without causing any troubles in health and displays said program as an ideal body weight transition curve as shown in FIG. 11. That is to say, the ideal body weight transition curve is plotted to show an ideal transition in body weight in order to achieve the target body weight according to the schedule relating to the matches or competitions without causing any troubles. FIG. 11 shows one ideal body weight transition curve for a user of boxing player who had conventionally repeated the weight reduction and gain as shown in FIG. 12, wherein the longitudinal axis represents a body weight and the lateral axis represents a month and day. As shown in FIG. 11, in the schedule relating to the matches for this user, the period from January to March is to be an off-season, from April to the end of November to be a match season with total of four matches each being arranged every two months starting at the end of May, and from the end of November forward to be another off-season, and the target body weight is 60 kg because the user is going to participate in all of the bouts in 60 kg class. His/her reference body weight at the present time of measurement in January is 65 kg. The body weight managing program is generated based on such a basic policy that, for example, the user practices the weight loss in a period starting in the off-season through to the beginning of the season allowing a margin of time for achieving the target body weight, maintains the achieved target body weight during the season, and is allowed to gain some weight within a range feasible to return back to the target weight in order to secure some mentally rest period during the off-season from the end of the season to the starting of the weight reduction in the following year. The weight reduction program to be practiced in the off-season is generated in such a way that, for example, after determining a volume of weight loss per week to be 0.9 kg, i.e., about 125 g for a volume of weight loss per day, which is in a reasonable range, the number of days required for the weight loss is calculated as 40 days from said determined value and a total volume of weight loss of 5 kg which is a difference between the target body weight and the reference body weight, and thus the program is generated so as to suggest "the weight loss of 125 g per day starting 40 days prior to the first day of the match season", as shown in FIG. 11. Thereafter, the user is allowed to reduce his weight on purpose with some margin according to thus determined ideal body weight transition curve.

Figure 13:
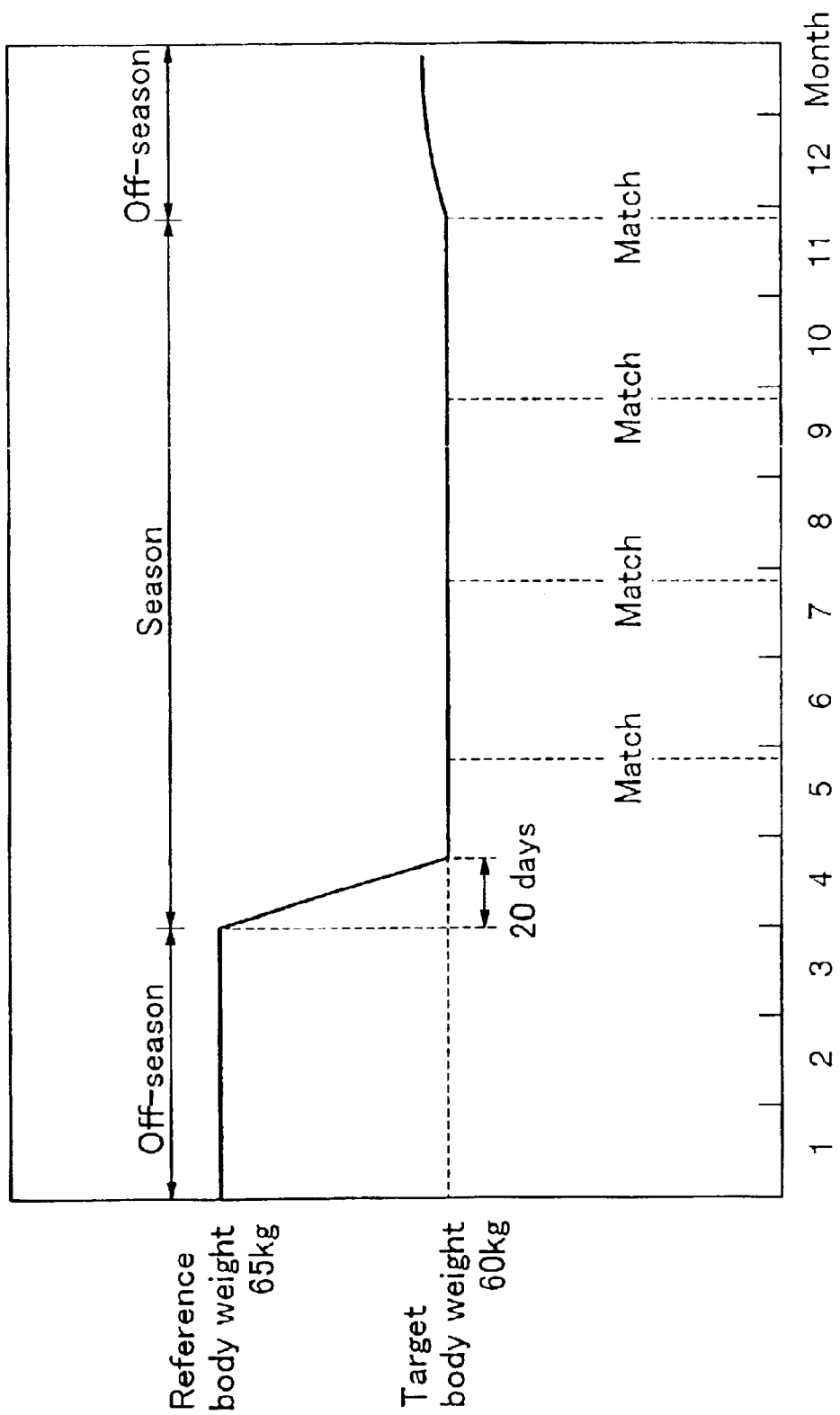
FIG. 13 is a diagram showing another example of a preferred body weight transition curve of the second embodiment.

However, especially in the off-season when the user is relieved, it often is the case that the weight loss is not achieved as expected. Accordingly, the managing apparatus regularly, after performing the measurement at Step S15, regenerates the body weight managing program by using the last measured body weight instead of the reference body weight and also regenerates the ideal body weight transition curve. The weight reduction program for this case may be generated based on such a basic policy that, for example, the weight reduction should be practiced to achieve the target body weight as early as possible within a reasonable range, allowing the user to concentrate to the training as much as possible. Then, if, for example, the user goes into the match season without having reduced his body weight of 65 kg, the weight reduction program is regenerated in such a way that after determining a volume of weight reduction per week to be 1.8 kg, i.e., about 250 g for a volume of weight reduction per day, which is a threshold value in a reasonable range, the number of days required for the weight reduction is calculated as 20 days from said determined value and the total volume of weight reduction of 5 kg which is a difference between the target body weight and the body weight at the present time, and thus the program is regenerated so as to suggest "the weight reduction of 250 g per day in 20 days from now on" and the ideal body weight transition curve is also regenerated as shown in FIG. 13.

Figure 14:
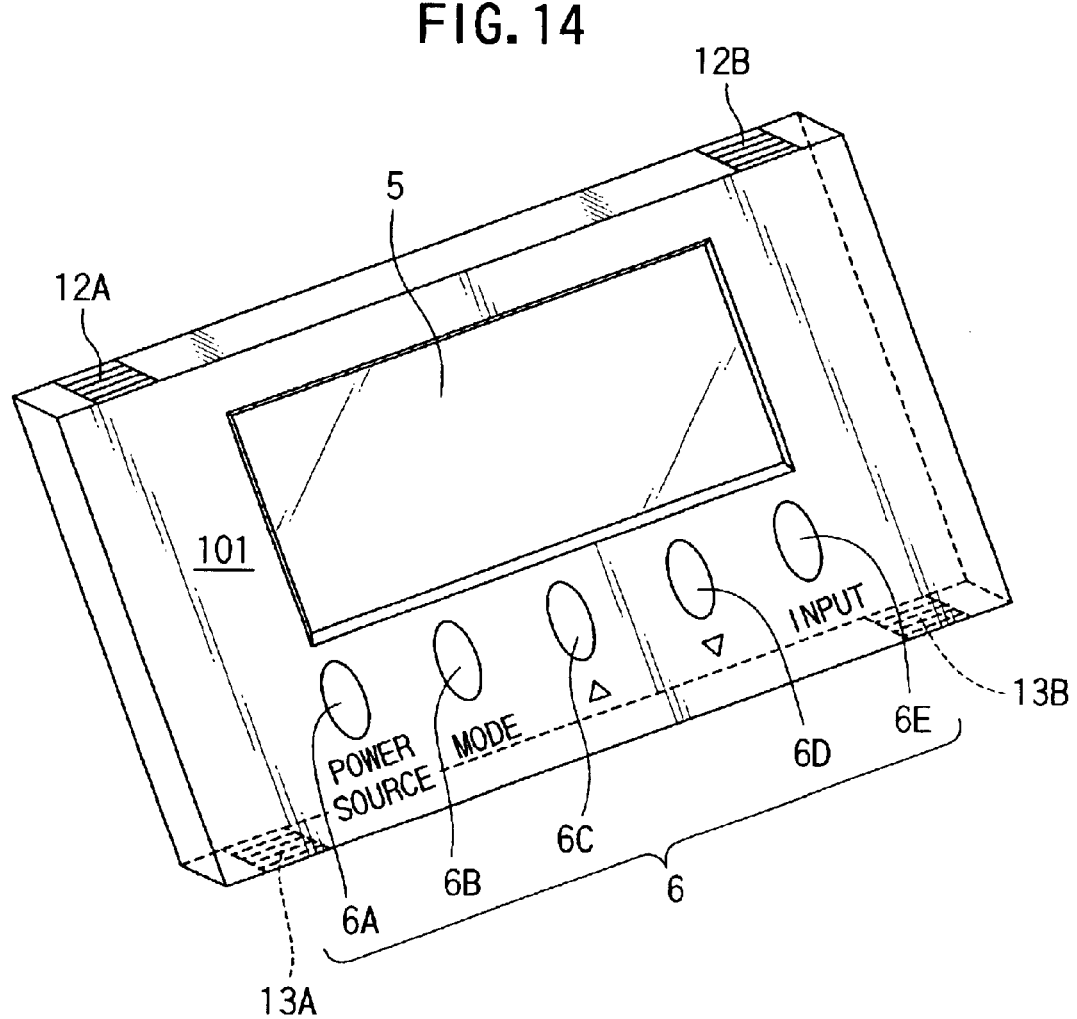
FIG. 14 is a perspective view illustrating an appearance of a body weight managing apparatus according to a third embodiment of the present invention.

FIG. 14 is a perspective view illustrating an appearance of a body weight managing apparatus according to a third embodiment of the invention. In FIG. 14, components corresponding to the components shown in FIG. 1 are indicated by same reference numerals used in FIG. 1. As shown in FIG. 14, the body weight managing apparatus according to the third embodiment of the invention is of a handheld type and comprises a main body 101 having a display section 5, a group of key switches 6 and an external I/O interface 7 (see FIG. 15), similarly to the control section of the first embodiment of FIG. 1. The key switches 6 include an electric power source switch 6A for supplying electricity to the body weight managing apparatus, a mode switch 6B, a up-switch 6C, a down-switch 6D and a input switch 6E. The power source switch 6A is mounted on a left lower portion of a front surface of the main body 101. The power source switch 6A is configured so that when the power source switch 6A is pushed once, the electricity is supplied and, when the power source switch 6A is pushed once again, the electricity is cut off. The mode switch 6B, the up-switch 6C, the down-switch 6D and the input switch 6E are arranged in line in this order on the right side of the power source switch 6A.

The mode switch 6B is configured so that when the mode switch 6B is pushed, a function of the body weight managing apparatus is switched among a body weight input mode for inputting a measured body weight, a measurement mode for measuring a bioelectric impedance using the data having been stored, a display mode for displaying guidance for measurement, evaluated result, estimated result, and the like.

The up-switch 6C increases a value of a displayed data when pushed repeatedly or continuously under the body weight input mode or the like. The down-switch 6D decreases a value of the displayed data having been increased by the up-switch 6C. The input switch 6E sends the displayed data set by the up-switch 6C and the down-switch 6D under each of the modes as a confirmed data to the auxiliary storage 8 of FIG. 15. The display section 5 for displaying a data set and inputted by the switches, a measured result, a guidance message for the measurement or the like is provided on an upper portion of the front surface of the main body 101.

The electrode 12A made of conductive metal chip or metal-plated material is provided near to a left end portion of an upper surface of the main body 101, and the electrode 12B made of the same material as of the electrode 12A is provided near to a right end portion of the upper surface. Though forefingers of the left and the right hands are typically brought into contact with the electrodes 12A and 12B respectively, a middle finger, a medical finger or a little finger may be used instead and the electrodes 12A and 12B are arranged placing a certain distance therebetween so that the finger of the left hand and that of the right hand may not come in contact with each other. The electrodes 13A and 13B are provided on a lower side surface of the main body 101 as the electrodes 12A and 12B are on the upper surface. Thumbs of the left and the right hands are brought into contact with the electrodes 13A and 13B respectively.

Figure 15:
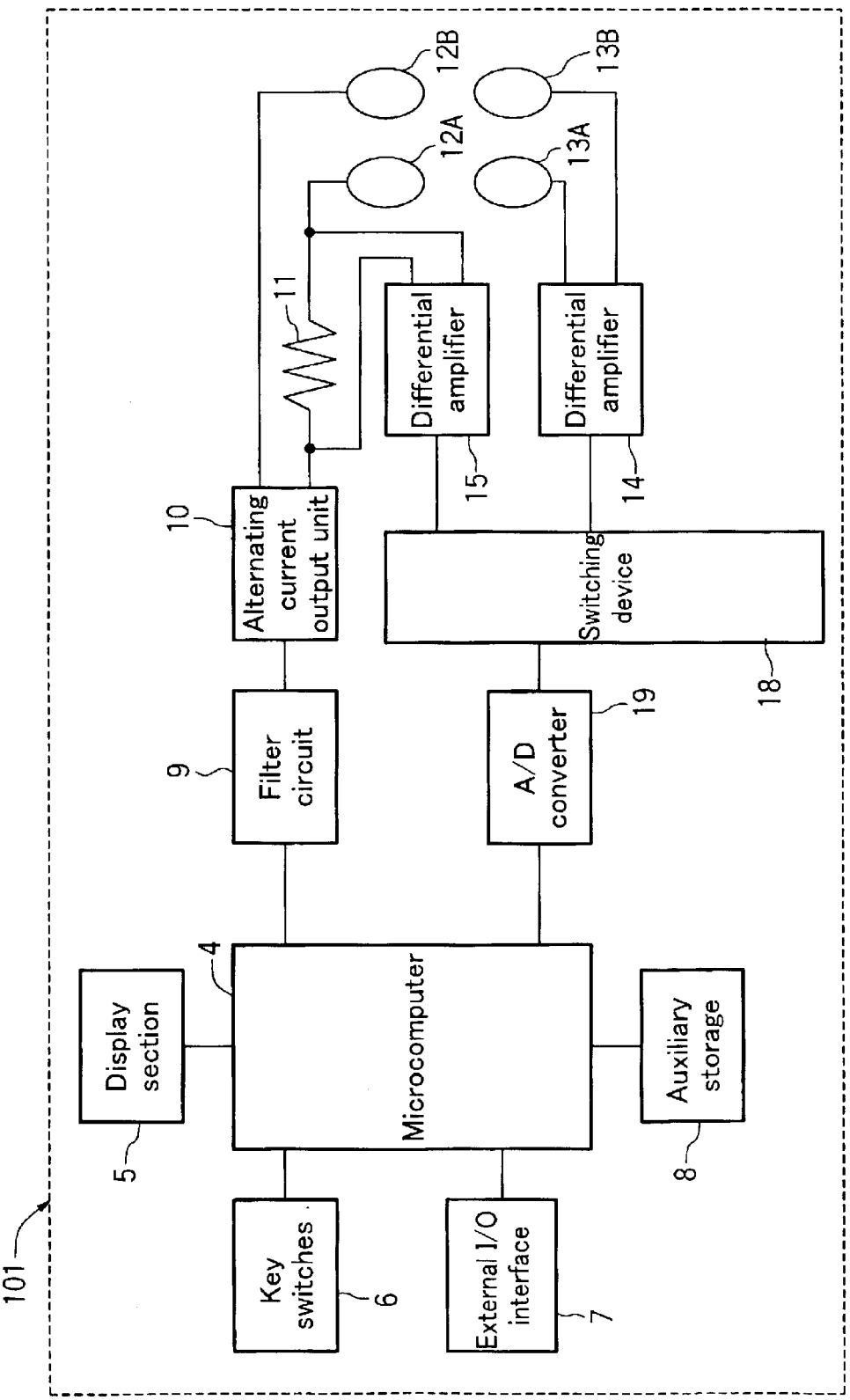
FIG. 15 is a schematic diagram illustrating an internal configuration of the third embodiment shown in FIG. 14.

FIG. 15 is a block diagram illustrating an internal configuration of the body weight managing apparatus shown in FIG. 14. In FIG. 15, components corresponding to the components shown in FIG. 2 are indicated by same reference numerals used in FIG. 2. As shown in FIG. 15, this body weight managing apparatus comprises a microcomputer 4 including a CPU for performing a control and an arithmetic operation concerning to a measurement or the like, a ROM for storing a control and an arithmetic program, constants and the like, a RAM for temporarily storing a calculated result, a program read from an external components, parameters and the like and further a timer, a clock for generating date information, an I/O port and the like, the display section 5 of a liquid-crystal display for indicating an personal parameter, a measured result, a measurement condition for a user, and the like, the key switches 6 used to turn on or off the power source to the managing apparatus, to input a control command and personal parameters including measured body weight and the like to this managing apparatus and to select the personal parameter stored in an auxiliary storage 8, an external I/O interface 7 for performing an input-output operation to the external component, and the nonvolatile auxiliary storage 8 capable of storing, reading and updating the personal parameter, other parameters concerning to the measurement and the like.

This body weight managing apparatus further comprises a filter circuit 9 for forming a signal output from the microcomputer 4 into a signal to be applied to a living body, an alternating current output unit 10 for processing a signal output from the filter circuit 9 to generate a regulated effective value, a reference resistance 11 connected to one of output terminals of the alternating current output unit 10 for detecting a current flowing through the body of the user, the alternating current supply electrode 12A connected to one of the output terminals of the alternating current output unit 10 via the reference resistance 11 for applying a measuring current to the user, the alternating current supply electrode 12B connected to another one of the output terminals of the alternating current output 10 for applying a measuring current to the user, a differential amplifier 15 for detecting a potential difference between both ends of the reference resistance 11, potential measuring electrodes 13A and 13B for detecting potentials in two sites of the user, a differential amplifier 14 connected to the potential measuring electrodes 13A and 13B for detecting a potential difference between those electrodes, a body weight, a switching unit 18 for selecting and outputting either one among those outputs from the differential amplifiers 15 and 14 based on a control by the microcomputer 4, and an A/D converter 19 for converting an analog signal representative of an output from the switching unit 18 into a digital signal and outputting the digital signal to the microcomputer 4.

Figure 16:
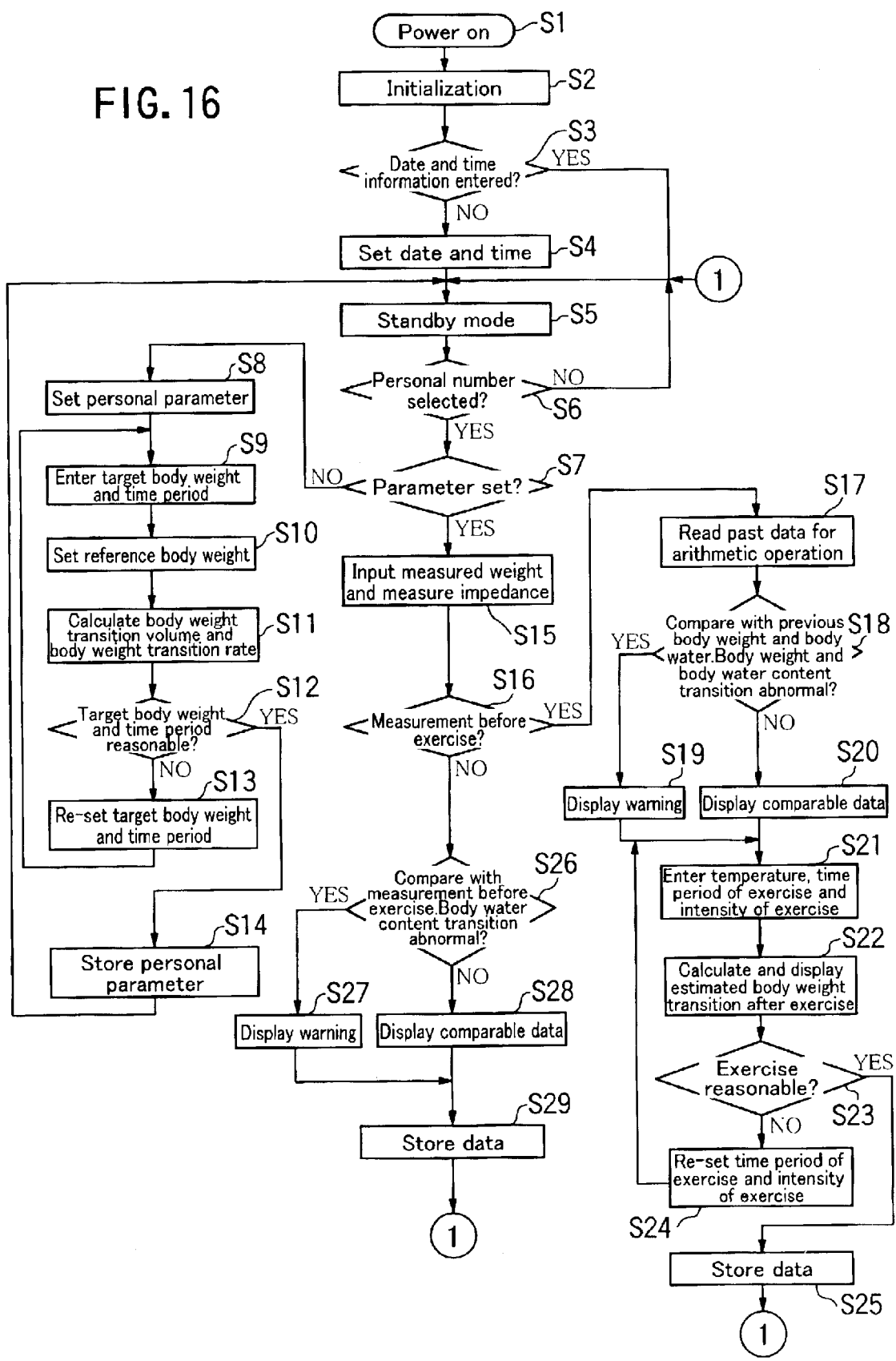
FIG. 16 is a flow chart illustrating an operational flow in the third embodiment shown in FIG. 14.

FIG. 16 is a flow chart illustrating an operational flow of the third embodiment. As seen from a comparison of FIGS.

1–6 with FIG. 3, the operation of the third embodiment is substantially identical with that of the first embodiment, except for the following points: In the third embodiment, in the step S15 a body weight as measured by a separate weighing scale is inputted to the body weight managing apparatus and a bioelectric impedance is measured by the body weight managing apparatus, while in the first embodiment, in the step S15 both of body weight and bioelectric impedance are measured by the managing apparatus. Inputting of the body weight measured by the separate scale can be effected in the following manner. The body weight managing apparatus is switched into a body weight input mode by use of the mode switch 6B, the numerical value representing the measured weight is set by use of the up-switch 6C and down-switch 6D and the set numerical value is inputted to the managing apparatus by use of the input switch 6E. Furthermore, in the third embodiment, to measure the impedance in the step S15, the user grasps the main body 101 of the managing apparatus with the chips of the forefingers or the middle fingers or the medical fingers or the little fingers of the left and right hands of the user contacting the alternating current supply electrodes 12A and 12B and the chips of the thumbs of the left and right hands of the user contacting the potential measuring electrodes 13A and 13B, while in the first embodiment, to measure the impedance in the step S15, the user stands on the measuring section 2 with the toe portions of bottoms of the left and right feet of the user contacting the alternating current supply electrodes 12A and 12B and the heel portions of bottoms of the left and right feet of the user contacting the potential measuring electrodes 13A and 13B.

Figure 17:
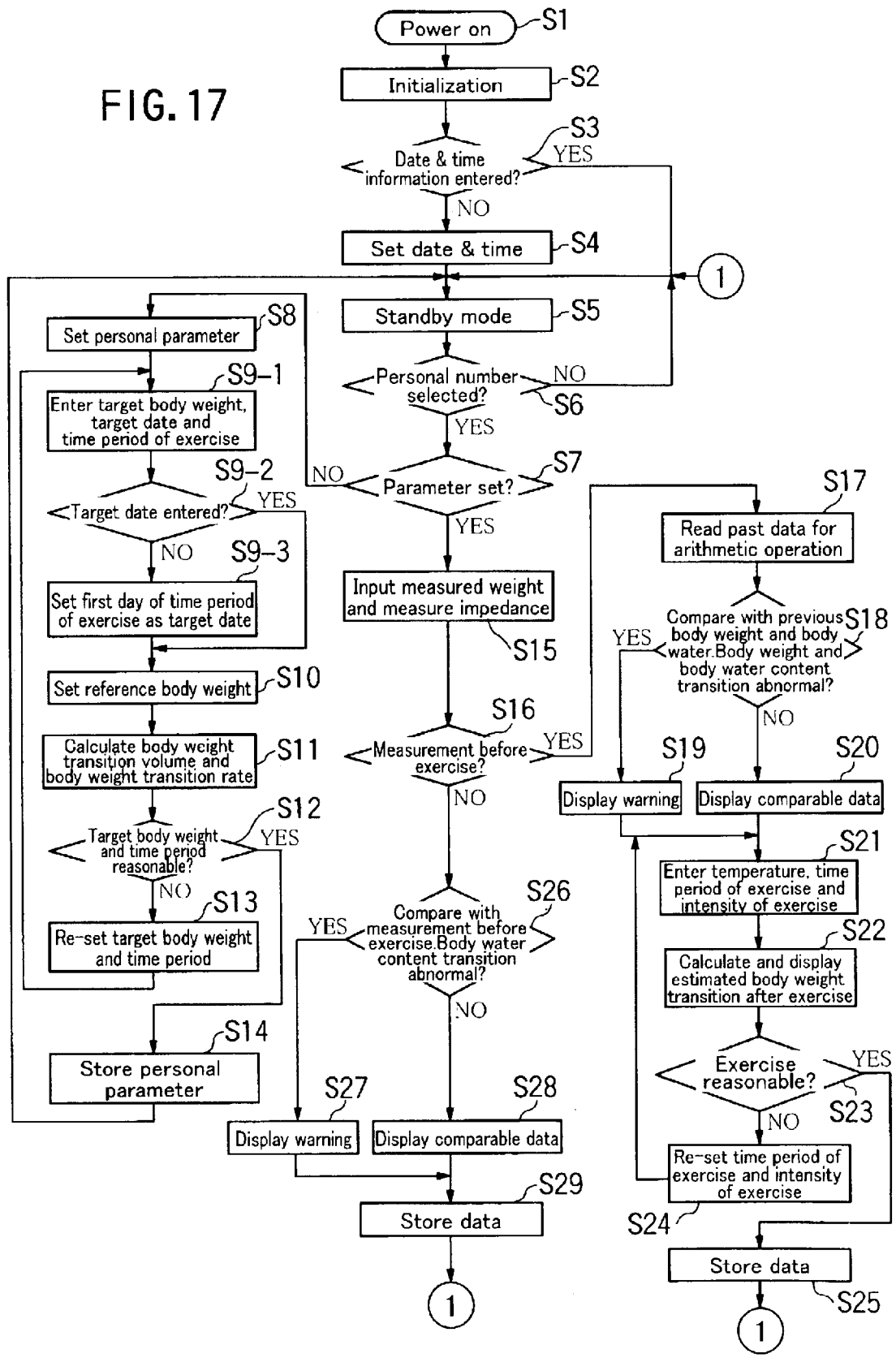
FIG. 17 is a flow chart illustrating an operational flow in a second embodiment.

Similarly to that the first embodiment of FIG. 1 may be used as the second embodiment to manage a body weight of a sport player for a long time period, for example, for a year, the third embodiment of FIG. 14 may be used as a fourth embodiment of the invention to make such management. FIG. 17 is a flow chart illustrating an operational flow of the fourth embodiment. As seen from a comparison of FIG. 17 with FIG. 9, the operation of the fourth embodiment is substantially identical with that of the second embodiment, except for the following points: In the fourth embodiment, in the step S15 a body weight as measured by a separate weighing scale is inputted to the body weight managing apparatus and a bioelectric impedance is measured by the body weight managing apparatus, while in the second embodiment, in the step S15 both of body weight and bioelectric impedance are measured by the managing apparatus. Inputting of the body weight measured by the separate scale can be effected in the following manner. The body weight managing apparatus is switched into a body weight input mode by use of the mode switch 6B, the numerical value representing the measured body weight is set by use of the up-switch 6C and down-switch 6D and the set numerical value is inputted to the managing apparatus by use of the input switch 6E. Furthermore, in the fourth embodiment, to measure the impedance in the step S15, the user grasps the main body 101 of the managing apparatus with the tips of the forefingers or the middle fingers or the medical fingers or the little fingers of the left and right hands of the user contacting the alternating current supply electrodes 12A and 12B and the tips of the thumbs of the left and right hands of the user contacting the potential measuring electrodes 13A and 13B, while in the second embodiment, to measure the impedance in the step S15, the user stands on the measuring section 2 with the toe portions of bottoms of the left and right feet of the user contacting the alternating current supply electrodes 12A and 12B and the heel portions of bottoms of the left and right feet of the user contacting the potential measuring electrodes 13A and 13B.

Although in the third and fourth embodiments described above, weight data and personal parameters are inputted by means of the key switches 6, these data may be inputted by connecting an external measuring device or a personal computer to the external I/O interface 7 directly or through a communication network such as Internet.

The contents of the steps other than Steps S9-1, 9-2, 9-3, S11 and S12 as described above are the same as those in the first embodiment.

It is to be noted that although the above explanation of the embodiment has mainly given to the case of weight loss, of course, the body weight managing apparatus of the second embodiment is also applicable to the case of weight gain similarly to the body weight managing apparatus of the first embodiment.

Although the first and the second embodiments of the present invention have been described in detail as above, the present invention is not limited to those embodiments. For example, the evaluation parameters and the evaluation criteria used to determine whether or not the target body weight and the target time period are unreasonable values, or to evaluate the condition of the body weight transition or the condition of the body water content are not limited to those which have been described above, but other evaluation parameters and other evaluation criteria based on the measured body weight and/or the bioelectric impedance value may be used, that is to say, other evaluation parameters and other evaluation criteria which use either of the measured body weight and/or the bioelectric impedance value themselves or any other values derived therefrom may be used. For example, the evaluation parameter for the condition of the body water content, other than that described in the present embodiment, may be at least one selected from a group consisting of body water content, intracellular fluid content, extracellular fluid content, a ratio of either one of those fluid volume to another one of those fluid volume, a combined intracellular and extracellular fluid resistance, intracellular fluid resistance, extracellular fluid resistance and a ratio of either one of those resistance to another one of those resistance, and all of those values may be determined from the bioelectric impedance values.

Alternatively, the condition of body weight transition and the condition of body water content may be combined to be used for comprehensively evaluating the health condition. There is one such example that combines a body weight transition rate of before to after the exercise, which is an evaluation parameter for the condition of the body weight transition, with an evaluation level, which is an evaluation parameter for the condition of the body water content, wherein the evaluation of the health is performed based on such an evaluation criterion that the cases having the body weight transition rate of before to after exercise of +2% and the evaluation level of +1, or the body weight transition rate of before to after exercise of −2% and the evaluation level of −1 are determined abnormal in health condition. Then, for the determined result which falls into, for example, the former case, the apparatus may display such a warning indication like "The intracellular fluid content is under increase, try to engage in athletic activities with sweating. Preferably, refrain from an intake of water.", and for the result of the latter case, it may displays such a warning indication like "With this condition of body water content to go on, there will be possibly appeared such symptoms as headache, higher rate in heart beat and breathing, rise in body temperature and the like in addition to a deterioration in athletic ability. Intake fluid containing electrolytes immediately, and fit yourself for exercise."

Further, in the above embodiments, merely a condition of the body weight transition has been evaluated at the point of time before the exercise and merely a condition of the body water content has been evaluated at the point of time after the exercise to evaluate the condition of health, but both of the condition of the body weight transition and the condition of the body water content may be evaluated at respective points of time.

Still further, in addition to those evaluations of the condition of the body weight transition and the condition of the body water content, other conditions of health, for example, a condition of body fat mass may be evaluated based on a measured body weight and bioelectric impedance value, that is, other evaluations may be performed by using the measured body weight and/or bioelectric impedance value themselves or any other values derived therefrom. In general, the condition of the body fat mass, similarly to the condition of the body water content, tends to be varied associated with the body weight transition, and said condition of the body fat mass also has important implications for one's health. Those evaluation parameter values such as a body fat ratio to be used for evaluating the condition of the body fat mass and the like may be derived from the measured bioelectric impedance value.

Further, although in the above embodiments, in order to indicate the condition of the body weight transition and/or the condition of the body water content to a user, the condition of the body weight transition and/or the condition of the body water content have been evaluated based on the measured body weight and/or the measured bioelectric impedance value and the determined result is indicated, alternatively those values representative of the condition of the body weight transition and/or the condition of the body water content for allowing the user to evaluate the condition of the body weight transition and/or the condition of the body water content may be derived from the measured body weight and/or the measured impedance values so as to be indicated to the user. The values representative of the condition of the body weight transition, which can be determined from the measured body weight, include for example, a body weight transition rate per day, a body weight transition volume per week, and a body weight measured on at least two points of time, and the values representative of the condition of the body water content, which can be derived from the measured bioelectric impedance value, include a body water content, a body water content transition volume, and body water contents, extracellular fluid contents, ratios of intracellular to extracellular fluid contents each being obtained on at least two points of time and the like.

As described above, the intention of the present invention is to indicate the condition of health such as the condition of the body weight transition and/or the condition of the body water content based on the measured body weight and/or the measured bioelectric impedance value, which includes the indication of a determined result for the health condition that has been determined based on the measured body weight and/or the measured bioelectric impedance value and/or other indication of a value representative of the health condition that has been determined based on the measured body weight and/or the measured bioelectric impedance value.

Further, in order to allow for any target changes and/or schedule changes, which may possibly occur after the target body weight, the target time period and the schedule relating to the matches or competitions having been entered, an apparatus of the present invention may be designed to allow those values to be occasionally changed so that whether or not a changed target body weight and/or a changed target time period may be determined unreasonable or so that a body weight managing program my be regenerated and an ideal body weight transition curve may be indicated, at each time when the values have been changed.

Further, at each time when the body weight is newly measured, the value may be used as a newly established reference body weight so as to determine whether or not the already set target body weight and time period are unreasonable values.

In addition, as to the schedule relating to the matches and competitions, for example, a pre-season, a day for measurement, a day for rest and the like may be entered.

Further, the generated body weight managing program may be indicated by way of a table, a text or the like.

Still further, a warning of, for example, abnormality in the condition of the body weight transition may be made by means of lump-lighting, voice, buzzer or the like.

Yet further, the bioelectric impedance value may be measured by using an alternating current of a single frequency.

As having been described above, according to the body weight managing apparatus of the present invention, since the body weight is allowed to be measured and indicated, and at the same time the condition of the body weight transition is determined based on the measured body weight, while the condition of the body water content is determined based on the measured bioelectric impedance value, and the determined results are accordingly indicated, therefore a user can check out adequately his/her health condition as well as body weight, and thereby can practice a weight reduction or gain in a reasonable way without doing any harm to health to achieve the targeted body weight.

Further, since it is determined whether or not the target body weight and the target time period required to achieve said target body weight are unreasonable values, and if determined unreasonable, a warning is given, therefore a user can avoid any unreasonable weight reduction or gain beforehand, and thereby also the user can practice the weight reduction or gain in a reasonable way without doing any harm to health to achieve the targeted body weight.

Still further, since the body weight managing program and the ideal body weight transition curve are generated and indicated based on the schedule relating to the matches or competitions and the reference body weight without giving any unreasonable requirements to health, a user can practice the weight reduction or gain in a reasonable way according to the managing program without doing any harm to health to achieve the targeted body weight.

It is to be noted that the present managing apparatus is useful to not only sports players but also ordinary people, and useful exclusively for the purpose of maintaining and managing one's health rather than the purpose of losing or gaining weight.

What is claimed is:

1. A body weight managing apparatus comprising:
   a first input unit;
   a clock;
   a second input unit;
   an arithmetic unit; and
   a setting unit; wherein
   said first input unit inputs a measured body weight of a person, said clock provides a clocking function, said second input unit enters a target body weight, a target date and a time period for exercise, said arithmetic unit produces a body weight managing data based on the difference between the measured body weight inputted by said first input unit and the target body weight entered by said second input unit, and the number of days remaining until the target date entered by said input unit, and said setting unit sets a first day of the time period of exercise as the target date if there is no target date entered.

2. A body weight managing apparatus according to claim 1 in which said first day of the time period of exercise is a start date of an exercise season.

3. A body weight managing apparatus according to claim 1 in which said first day of the time period of exercise is a day on which a match or competition is conducted.

4. A body weight managing apparatus comprising:
a first input unit;
a clock;
a second input unit;
an arithmetic unit; and
a setting unit; wherein
said first input unit inputs a measured body weight of a person, said clock provides a clocking function, said second input unit enters a target body weight, a target date and a time period for exercise, said arithmetic unit produces a body weight managing data based on the difference between the measured body weight inputted by said first input unit and the target body weight entered by said second input unit, and the number of days remaining until the target date entered by said input unit, and said setting unit sets a first day of the time period of exercise as the target date if there is no target date entered.

5. A body weight managing apparatus according to claim 4 in which said first day of the time period of exercise is a start date of exercise season.

6. A body weight managing apparatus according to claim 4 in which said first day of the time period of exercise is a day on which a match or competition is conducted.

7. A body weight managing apparatus comprising:
a body weight input unit;
a bioelectric impedance measuring unit;
a body weight water content evaluation unit, and
a health condition evaluation unit,
wherein said body weight input unit inputs a measured body weight of a person, said bioelectric impedance measuring unit applies an alternating current to a body of the person and measures a bioelectric impedance value, said body water content evaluation unit evaluates a body water content based on the bioelectric impedance value measured by said bioelectric impedance measuring unit, and said health condition evaluation unit evaluates a health condition of the person based on the measured body weight inputted by said body weight input unit and the evaluation from said body water content evaluation unit, and
wherein said health condition evaluation unit evaluates based on a combination of body weight transition and body water content transition as measured for a period of plural days;
the apparatus further comprising a data input unit and a body weight estimation unit;
wherein said data input unit enters data relating to an exercise, and said body weight estimation unit estimates a body weight after the exercise based on the measured body weight inputted by said body weight input unit and the data entered by said data input unit.

8. A body weight managing apparatus according to claim 7, wherein said input unit enters at least one of temperature, time period of exercise and intensity of exercise.

9. A body weight managing apparatus comprising:
a body weight input unit;
a bioelectric impedance measuring unit;
a body weight water content evaluation unit, and
a health condition evaluation unit,
wherein said body weight input unit inputs a measured body weight of a person, said bioelectric impedance measuring unit applies an alternating current to a body of the person and measures a bioelectric impedance value, said body water content evaluation unit evaluates a body water content based on the bioelectric impedance value measured by said bioelectric impedance measuring unit, and said health condition evaluation unit evaluates a health condition of the person based on the measured body weight inputted by said body weight input unit and the evaluation from said body water content evaluation unit, and
wherein said health condition evaluation unit evaluates based on a combination of body weight transition and body water content transition as measured for a period of plural days;
the apparatus further comprising a second input unit, an arithmetic unit, and a setting unit;
wherein said second input unit enters a target body weight, a target date and a time period for exercise, said arithmetic unit produces a body weight managing data based on the difference between the measured body weight inputted by said weight input unit and the target body weight entered by said second input unit, and the number of days remaining until the target date entered by said input unit, and said setting unit sets a first day of the time period of exercise as the target date if there is no target date entered.

10. A body weight managing apparatus according to claim 9, wherein said first day of the time period of exercise is a start date of an exercise season.

11. A body weight managing apparatus according to claim 9, wherein said first day of the time period of exercise is a day on which a match or competition is conducted.

12. A body weight managing apparatus comprising:
a body weight input unit;
a bioelectric impedance measuring unit;
a body weight water content evaluation unit, and
a health condition evaluation unit,
wherein said body weight input unit inputs a measured body weight of a person, said bioelectric impedance measuring unit applies an alternating current to a body of the person and measures a bioelectric impedance value, said body water content evaluation unit evaluates a body water content based on the bioelectric impedance value measured by said bioelectric impedance measuring unit, and said health condition evaluation unit evaluates a health condition of the person based on the measured body weight inputted by said body weight input unit and the evaluation result from said body water content evaluation unit, and
wherein said health condition evaluation unit evaluates based on a combination of body weight transition and body water content transition as measured for a period of plural days;

the apparatus further comprising a data input unit and a body weight estimation unit;

wherein said data input unit enters data relating to an exercise, and said body weight estimation unit estimates a body weight after the exercise based on the measured body weight inputted by said body weight input unit and the data entered by said data input unit.

13. A body weight managing apparatus according to claim 12, wherein said input unit enters at least one of temperature, time period of exercise and intensity of exercise.

14. A body weight managing apparatus comprising:
a body weight input unit;
a bioelectric impedance measuring unit;
a body weight water content evaluation unit, and
a health condition evaluation unit,
wherein said body weight input unit inputs a measured body weight of a person, said bioelectric impedance measuring unit applies an alternating current to a body of the person and measures a bioelectric impedance value, said body water content evaluation unit evaluates a body water content based on the bioelectric impedance value measured by said bioelectric impedance measuring unit, and said health condition evaluation unit evaluates a health condition of the person based on the measured body weight inputted by said body weight input unit and the evaluation result from said body water content evaluation unit, and wherein said health condition evaluation unit evaluates based on a combination of body weight transition and body water content transition as measured for a period of plural days;

the apparatus further comprising a second input unit, an arithmetic unit, and a setting unit;

wherein said second input unit enters a target body weight, a target date and a time period for exercise, said arithmetic unit produces a body weight managing data based on the difference between the measured body weight inputted by said weight input unit and the target body weight entered by said second input unit, and the number of days remaining until the target date entered by said input unit, and said setting unit sets a first day of the time period of exercise as the target date if there is no target date entered.

15. A body weight managing apparatus according to claim 14, wherein said first day of the time period of exercise is a start date of an exercise season.

16. A body weight managing apparatus according to claim 14, wherein said first day of the time period of exercise is a day on which a match or competition is conducted.

* * * * *

UNITED STATES PATENT AND TRADEMARK OFFICE
CERTIFICATE OF CORRECTION

PATENT NO. : 6,963,035 B2
DATED : November 8, 2005
INVENTOR(S) : Yuka Honda et al.

It is certified that error appears in the above-identified patent and that said Letters Patent is hereby corrected as shown below:

<u>Title page,</u>
Item [30], Foreign Application Priority Data, change "Aug. 4, 2000 (JP).........2002-237190" to -- Aug. 4, 2000 (JP).............2000-237190 --.

Signed and Sealed this

Second Day of May, 2006

JON W. DUDAS
*Director of the United States Patent and Trademark Office*